(12) United States Patent
Fischer et al.

(10) Patent No.: US 10,364,274 B2
(45) Date of Patent: Jul. 30, 2019

(54) EXPRESSION OF CHIMERIC KSAC PROTEIN AND METHOD OF PRODUCING SOLUBLE PROTEINS BY HIGH PRESSURE

(71) Applicant: BOEHRINGER INGELHEIM ANIMAL HEALTH USA INC., Duluth, GA (US)

(72) Inventors: Laurent Bernard Fischer, Saint Foy les Lyon (FR); Nicolas Pierre Yves Carboulec, Saint Goueno (FR); Fabien Lux, Saint-Priest (FR)

(73) Assignee: BOEHRINGER INGELHEIM ANIMAL HEATLH USA INC., Duluth, GA (US)

( * ) Notice: Subject to any disclaimer, the term of this patent is extended or adjusted under 35 U.S.C. 154(b) by 93 days.

(21) Appl. No.: 15/017,486

(22) Filed: Feb. 5, 2016

(65) Prior Publication Data
US 2017/0081372 A1    Mar. 23, 2017

Related U.S. Application Data

(63) Continuation of application No. 14/014,437, filed on Aug. 30, 2013, now Pat. No. 9,315,553.

(60) Provisional application No. 61/694,968, filed on Aug. 30, 2012, provisional application No. 61/830,425, filed on Jun. 3, 2013.

(51) Int. Cl.
| | |
|---|---|
| *A61K 39/00* | (2006.01) |
| *A61K 39/002* | (2006.01) |
| *C07K 14/245* | (2006.01) |
| *A23L 3/015* | (2006.01) |
| *A61K 39/008* | (2006.01) |
| *A61K 39/02* | (2006.01) |
| *A61L 2/00* | (2006.01) |
| *C12N 9/10* | (2006.01) |
| *C12N 9/52* | (2006.01) |
| *C07K 14/44* | (2006.01) |
| *C12N 9/50* | (2006.01) |
| *C12N 5/00* | (2006.01) |
| *C12P 21/02* | (2006.01) |

(52) U.S. Cl.
CPC .......... *C07K 14/245* (2013.01); *A23L 3/0155* (2013.01); *A61K 39/008* (2013.01); *A61K 39/0225* (2013.01); *A61K 39/0241* (2013.01); *A61K 39/099* (2013.01); *A61L 2/0011* (2013.01); *C07K 14/44* (2013.01); *C12N 9/1007* (2013.01); *C12N 9/50* (2013.01); *C12N 9/52* (2013.01); *C12Y 201/01041* (2013.01); *C12Y 304/22* (2013.01); *A61K 2039/552* (2013.01); *C07K 2319/00* (2013.01); *C07K 2319/35* (2013.01); *C07K 2319/40* (2013.01); *C12N 5/0031* (2013.01); *C12P 21/02* (2013.01)

(58) Field of Classification Search
CPC ..... A61K 38/00; C07K 14/44; C07K 2319/00
See application file for complete search history.

(56) References Cited

U.S. PATENT DOCUMENTS

| | | |
|---|---|---|
| 6,489,450 B2 | 12/2002 | Randolph |
| 7,064,192 B2 | 6/2006 | Randolph |
| 7,538,198 B2 | 5/2009 | Randolph |
| 7,615,617 B2 | 11/2009 | Robinson |
| 7,767,795 B2 | 8/2010 | Randolph |
| 7,829,681 B2 | 11/2010 | Seefeldt |
| 8,273,561 B2 | 9/2012 | Cleland |
| 8,329,878 B2 | 12/2012 | Randolph |
| 8,410,258 B2 * | 4/2013 | Goto .................... A61K 39/008 424/192.1 |
| 8,911,746 B2 * | 12/2014 | Goto .................... A61K 39/008 424/191.1 |
| 2009/0291099 A1 * | 11/2009 | Goto .................... A61K 39/008 424/192.1 |
| 2010/0136046 A1 * | 6/2010 | Goto .................... A61K 39/008 424/198.1 |
| 2014/0065187 A1 * | 3/2014 | Carboulec .......... A61K 39/0225 424/254.1 |
| 2016/0000896 A1 * | 1/2016 | Carboulec ............ A61K 39/099 424/254.1 |

FOREIGN PATENT DOCUMENTS

| | | |
|---|---|---|
| EP | 1 095 056 | 12/2006 |
| WO | WO2002/062827 | 8/2002 |
| WO | WO2009/143006 | 11/2009 |

OTHER PUBLICATIONS

Courtenay O. et al., "Infectiousness in a cohort of Brazilian dogs: why culling fails to control visceral Leishmaniasis in areas of high transmission", 2002, J. Infect. Dis., 186 :1314-20.

(Continued)

*Primary Examiner* — Gary B Nickol
*Assistant Examiner* — Lakia J Jackson-Tongue
(74) *Attorney, Agent, or Firm* — Judy Jarecki-Black; Steffan Finnegan

(57) ABSTRACT

The present invention encompasses vaccines or compositions comprising the chimeric KSAC protein that possesses immunogenic and protective properties, and methods of use including administering to an animal the antigenic KSAC protein thereof to protect animals. The invention also encompasses methods for making and producing the soluble, disaggregated, refolded or active proteins from inclusion bodies produced from prokaryotes or eukaryotes.

10 Claims, 29 Drawing Sheets

Specification includes a Sequence Listing.

(56) References Cited

OTHER PUBLICATIONS

Dietze R. et al., "Effect of eliminating seropositive canines on the transmission of visceral Leishmaniasis in Brazil", 1997, Clin. Infect. Dis. 25:1240-2.

Dye C., "The logic of visceral leishmaniasis control", 1996, Am. J. Trop. Med. Hyg. 55:125-30.

Gordon W. Niven et al., "The effect of hydrostatic pressure on ribosome conformation in *Escherichia coli*: an in vivo study using differential scanning calorimetry", 1999, Microbiology, 145, 419-425.

Gradoni L. et al., "Failure of a milti-subunit recombinant leishmanial vaccine (MML) to protect dogs from Leishmania infantum infection and to prevent disease progression in infected animals", 2005, Vacine 23:5245-51.

Grosjean NL et al., "Seroprevalence of antibodies against *Leishmania* spp among dogs in the United States", 2003, J Am Vet Med Assoc 222:603-606.

Fradkin et al., "Recombinant murine growth hormone from *E. coli* inclusion bodies: expression, high-pressure solubilization and refolding, and characterization of activity and structure", 2010, Biotechnol. Prog., vol. 26, No. 3, 743-749.

Lindsay DS et al., "Leishmaniasis in American foxhounds: an emerging zoonosis?", 2002, Compend Cont Educ Pract Vet 24:304-312.

Maroli M. et al., "Evidence for an impact on the incidence of canine leishmaniasis by the mass use of deltamethrin-impregnated dog collars in southern Italy", 2001, Med. Vet. Entomol. 15:358-63.

Martínez-Subiela S et al., "Serum concentrations of acute phase proteins in dogs with leishmaniasis", 2002, Vet Rec 150:241-244.

Masson Patrick et al., "High-pressure biotechnology in medicine and pharmaceutical science", 2001, Journal of Biomedicine and Biotechnology, 1:2, 85-88.

Mazloumi Gavgani A.S. et al., "Effect of insecticide-impregnated dog collars on incidence of zoonotic visceral leishmaniasis in Iranin children: a matched-cluster randomised trial", 2002, Lancet 360,374-9.

McConkey SE et al., "Leishmanial polyarthritis in a dog", 2002, Canine Vet J 43:607-609.

Molina R. et al., "Infectivity of dogs naturally infected with Leishmania infantum to colonized phlebotomus perniciosus", 1994, Trans. R. Soc. Med. Hyg. 88:491-3.

Moreira Jr. E.D. et al., "Assessment of an optimized dog-culling program in the dynamics of canine Leishmania transmission", 2004, Vet. Parasitol. 122:245-52.

Slappendel RJ et al., 1998, In: Greene CE: Infectious Diseases of the Dog and Cat, pp. 450-458.

Qoronfleh et al., 2007, "Confronting high-throughput protein refolding using high pressure and solution screes", Protein Expression and Purification, 55 (2) P209-224.

\* cited by examiner

Figure 1

| SEQ ID NO: | Type | Gene Description |
|---|---|---|
| 1 | DNA | KSAC DNA |
| 2 | protein | Chimeric KSAC protein |
| 3 | protein | Leishmania KMP11 protein |
| 4 | protein | Leishmania SMT protein |
| 5 | protein | Leishmania A2 protein |
| 6 | protein | Leishmania CBP protein |

Figure 2A

KSAC DNA sequence (SEQ ID NO:1)
ATGGCCACCACGTACGAGGAGTTTTCGGCGAAGCTGGACCGCCTGGATGAGGAGTTCAAC
AGGAAGATGCAGGAGCAGAACGCCAAGTTCTTTGCGGACAAGCCGGATGAGTCGACGCTG
TCGCCCGAGATGAAGGAGCACTACGAGAAGTTCGAGCGCATGATCAAGGAACACACAGAG
AAGTTCAACAAGAAGATGCACGAGCACTCGGAGCACTTCAAGCAGAAGTTCGCCGAGCTG
CTCGAGCAGCAGAAGGCTGCGCAGTACCCGTCCAAGACTAGTTCCGCCGGTGGCCGTGAG
ACCGCGCCGACGAACCTGATTCGTCGCCGCAACAAGGACGAGACAAACGGGGATGTCAGC
GCCGCCGCCGACCGCTTCCGCGACCGCTTCGAGAAGGCAACCCTCGAGGAGCGCAAGGCC
GCCACCACGACGATGGTCAACGAGTACTACGACCTGGTGACGGACTTCTACGAGTACGGC
TGGGGCCAGAACTTCCATTTCGCGCCGCGCTACGCCGGCGAGACCTTCTTCGAGTCCCTC
GCGCGCCACGAGTACTTCCTGGCCGCTCGCGGCGGCTTCATGGAGGGCGACCACATCGTC
GACGTGGGCTGCGGCGTCGGCGGTCCGGCGCGCAACATGGTTCGCCTCACGCGCTGCAAC
GTCATCGGCGTCAACAACAACGATTACCAGATCAGCCGCGCTCGCCGTCATGACGCGCTC
GCCGGTATGAGCTCCAAGATCGACTACGTCAAGACCGACTTCTGCAACATGAGCTTAGCC
GACAACACCTTCGACGGCGCCTACGCCATCGAGGCCACCTGCCACGCAAAGGACAAGGTC
AAGTGCTATAGCGAGGTCTTCCGTGTCATCAAGCCCGGCACCTGCTTTGTCCTGTACGAG
TGGTGCATGACCGACAAGTACAACCCCAATGACGAGTACCACCGCACAATCAAGCACCGC
ATCGAGCTGGGCGACGGCCTGCCGGAGATGGAGACGTGCAAACAGGTGATCGAGTACATG
AAGCAGGCCGGCTTCGTGGTGGAGGAGGCCATAGACGTCATCAGTCAGTTCGAGTCCAGC
CCCATCAAGAGTATCCCGTGGTACCAGCCGCTGGTCGGCGACTATTCGTCCCTGCAGGGC
CTGCGCTCTACCCCGATTGGCCGCATCCTCACGAACGTCATGTGTCGCGTGCTGGAGTTC
GTGCGCCTAGCTCCGAAGGGCACGTACAAGGCGACGGAGATTTTGGAGGAGGCTGCGGAA
AGCCTGGTGGTGGGCGGTCAGCTCGGCATCTTCACGCCGTCCTTCTACATCCGCGCTCGC
AAGCCGTCCAAGCAGGCTGGATCCAAGATCCGCAGCGTGCGTCCGCTTGTGGTGTTGCTG
GTGTGCGTCGCGGCGGTGCTCGCACTCAGCGCCTCCGCTGAGCCGCACAAGGCGGCCGTT
GACGTCGGCCCGCTGAGCGTTGGCCCGCAGAGCGTCGGCCCGCTGAGCGTTGGCCCGCAG
GCGGTTGGCCCGCTGAGCGTTGGCCCGCAGAGCGTCGGCCCGCTGAGCGTTGGCCCGCAG
GCGGTTGGCCCGCTGAGCGTTGGCCCGCAGAGCGTTGGCCCGCTGAGCGTTGGCCCGCTG
AGCGTTGGCCCGCAGAGCGTTGGCCCGCTGAGCGTTGGCAGCCAGAGCGTCGGCCCGCTG
AGCGTTGGTCCGCAGAGCGTCGGCCCGCTGAGCGTTGGCCCGCAGGCGGTTGGCCCGCTG
AGCGTTGGCCCGCAGAGCGTCGGCCCGCTGAGCGTTGGCCCGCAGGCGGTTGGCCCGCTG
AGCGTTGGCCCGCAGAGCGTTGGCCCGCTGAGCGTTGGCCCGCAGAGCGTTGGCCCGCTG
AGCGTTGGCAGCCAGAGCGTCGGCCCGCTGAGCGTTGGTCCGCAGAGCGTCGGCCCGCTG
AGCGTTGGCCCGCAGAGCGTCGGCCCGCTGAGCGTTGGCCCGCAGAGCGTCGGCCCGCTG
AGCGTTGGTCCGCAGAGCGTTGGCCCGCTGAGCGTTGGCCCGCAGAGCGTTGACGTTAGC
CCGGTGAGCGGATCCGAATTCGATGCGGTGGACTGGCGCGAGAAGGGCGCCGTGACGCCG
GTGAAGAATCAAGGCGCGTGCGGGTCGTGCTGGGCGTTCTCGGCGGTCGGCAACATCGAG
TCGCAGTGGGCCCGTGCCGGCCACGGCTTGGTGAGCCTGTCGGAGCAGCAGCTGGTGAGC
TGCGATGACAAAGACAATGGCTGCAACGGCGGGCTGATGCTGCAGGCGTTCGAGTGGCTG
CTGCGACACATGTACGGGATCGTGTTCACGGAGAAGAGCTACCCCTACACGTCCGGCAAC
GGTGATGTGGCCGAGTGCTTGAACAGCAGTAAACTCGTTCCCGGCGCGCAAATCGACGGC
TACGTGATGATCCCGAGCAACGAAACGGTTATGGCTGCGTGGCTTGCGGAGAATGGCCCC
ATCGCGATTGCGGTCGAC

Figure 2B

```
GCCAGCTCCTTCATGTCTTACCAGAGCGGCGTGCTGACCAGCTGCGCTGGCGATGCACTG
AACCACGGCGTGCTGCTCGTCGGGTACAACAAGACCGGTGGGGTTCCGTACTGGGTGATC
AAGAACTCGTGGGGTGAGGACTGGGGCGAGAAGGGCTACGTGCGCGTGGTCATGGGCTG
AACGCGTGCCTGCTCAGTGAATACCCCGTGTCCGCGCATGTGCCGCGGAGTCTCACCCCT
GGCCCGGGCACGGAGAGCGAGGAGCGCGCCCCTAAACGGGTGACGGTGGAGCAGATGATG
TGCACCGATATGTACTGCAGGGAGGGGTGCAAGAAGAGTCTTCTCACCGCGAACGTGTGC
TACAAGAACGGGGGAGGCGGCTCCTCTATGACGAAGTGCGGTCCGCAGAAGGTGCTGATG
TGCTCGTACTCGAACCCTCATTGCTTTGGTCCTGGGCTGTGCCTCGAGACTCCTGATGGC
AAGTGCGCGCCGTACTTCTTGGGCTCGATCATGAACACCTGCCAGTACACGTAA
```

KSAC protein sequence (SEQ ID NO:2)

MATTYEEFSAKLDRLDEEFNRKMQEQNAKFFADKPDESTLSPEMKEHYEKF
ERMIKEHTEKFNKKMHEHSEHFKQKFAELLEQQKAAQYPSK*TS*SAGGRET
APTNLIRRRNKDETNGDVSAAADRFRDRFEKATLEERKAATTTMVNEYYDL
VTDFYEYGWGQNFHFAPRYAGETFFESLARHEYFLAARGGFMEGDHIVDV
GCGVGGPARNMVRLTRCNVIGVNNNDYQISRARRHDALAGMSSKIDYVKT
DFCNMSLADNTFDGAYAIEATCHAKDKVKCYSEVFRVIKPGTCFVLYEWCM
TDKYNPNDEYHRTIKHRIELGDGLPEMETCKQVIEYMKQAGFVVEEAIDVIS
QFESSPIKSIPWYQPLVGDYSSLQGLRSTPIGRILTNVMCRVLEFVRLAPKGT
YKATEILEEAAESLVVGGQLGIFTPSFYIRARKPSKQA*GS*KIRSVRPLVVLLV
CVAAVLALSASAEPHKAAVDVGPLSVGPQSVGPLSVGPQAVGPLSVGPQSVG
PLSVGPQAVGPLSVGPQSVGPLSVGPLSVGPQSVGPLSVGSQSVGPLSVGPQS
VGPLSVGPQAVGPLSVGPQSVGPLSVGPQAVGPLSVGPQSVGPLSVGPQSVG
PLSVGSQSVGPLSVGPQSVGPLSVGPQSVGPLSVGPQSVGPLSVGPQSVGPLS
VGPQSVDVSPVS*GSEF*DAVDWREKGAVTPVKNQGACGSCWAFSAVGNIESQ
WARAGHGLVSLSEQQLVSCDDKDNGCNGGLMLQAFEWLLRHMYGIVFTE
KSYPYTSGNGDVAECLNSSKLVPGAQIDGYVMIPSNETVMAAWLAENGPIAI
AVDASSFMSYQSGVLTSCAGDALNHGVLLVGYNKTGGVPYWVIKNSWGED
WGEKGYVRVVMGLNACLLSEYPVSAHVPRSLTPGPGTESEERAPKRVTVEQ
MMCTDMYCREGCKKSLLTANVCYKNGGGGSSMTKCGPQKVLMCSYSNPH
CFGPGLCLETPDGKCAPYFLGSIMNTCQYT

- KPM11 (in red)
- Sterol Methyltransferase (in green)
- A2 (in blue).
- Cysteine proteinase (in brown)
- Linkers (in italic and black)

Figure 2C

KMP11 protein (SEQ ID NO:3)
MATTYEEFSAKLDRLDEEFNRKMQEQNAKFFADKPDESTLSPEMKEHYEKF
ERMIKEHTEKFNKKMHEHSEHFKQKFAELLEQQKAAQYPSK SMT protein (SEQ ID NO:4)
SAGGRETAPTNLIRRRNKDETNGDVSAAADRFRDRFEKATLEERKAATTTM
VNEYYDLVTDFYEYGWGQNFHFAPRYAGETFFESLARHEYFLAARGGFME
GDHIVDVGCGVGGPARNMVRLTRCNVIGVNNNDYQISRARRHDALAGMSS
KIDYVKTDFCNMSLADNTFDGAYAIEATCHAKDKVKCYSEVFRVIKPGTCF
VLYEWCMTDKYNPNDEYHRTIKHRIELGDGLPEMETCKQVIEYMKQAGFV
VEEAIDVISQFESSPIKSIPWYQPLVGDYSSLQGLRSTPIGRILTNVMCRVLEF
VRLAPKGTYKATEILEEAAESLVVGGQLGIFTPSFYIRARKPSKQA A2 protein (SEQ ID NO:5)
<u>KIRSVRPLVVLLVCVAAVLALSASAE</u>PHKAAVDVGPLSVGPQSVGPLSVGPQ
AVGPLSVGPQSVGPLSVGPQAVGPLSVGPQSVGPLSVGPLSVGPQSVGPLSV
GSQSVGPLSVGPQSVGPLSVGPQAVGPLSVGPQSVGPLSVGPQAVGPLSVGP
QSVGPLSVGPQSVGPLSVGSQSVGPLSVGPQSVGPLSVGPQSVGPLSVGPQSV
GPLSVGPQSVGPLSVGPQSVDVSPVS CBP protein (SEQ ID NO:6)
DAVDWREKGAVTPVKNQGACGSCWAFSAVGNIESQWARAGHGLVSLSEQQ
LVSCDDKDNGCNGGLMLQAFEWLLRHMYGIVFTEKSYPYTSGNGDVAECL
NSSKLVPGAQIDGYVMIPSNETVMAAWLAENGPIAIAVDASSFMSYQSGVLT
SCAGDALNHGVLLVGYNKTGGVPYWVIKNSWGEDWGEKGYVRVVMGLN
ACLLSEYPVSAHVPRSLTPGPGTESEERAPKRVTVEQMMCTDMYCREGCK
KSLLTANVCYKNGGGGSSMTKCGPQKVLMCSYSNPHCFGPGLCLETPDGK
CAPYFLGSIMNTCQYT Refolding of KSAC SDS-PAGE pattern of KSAC protein
refolded by exclusion chromatography HPLC plot of refolded KSAC by exclusion chromatography Dynamic Light Scattering (DLS) of refolded KSAC protein
using exclusion chromatography Figure 13
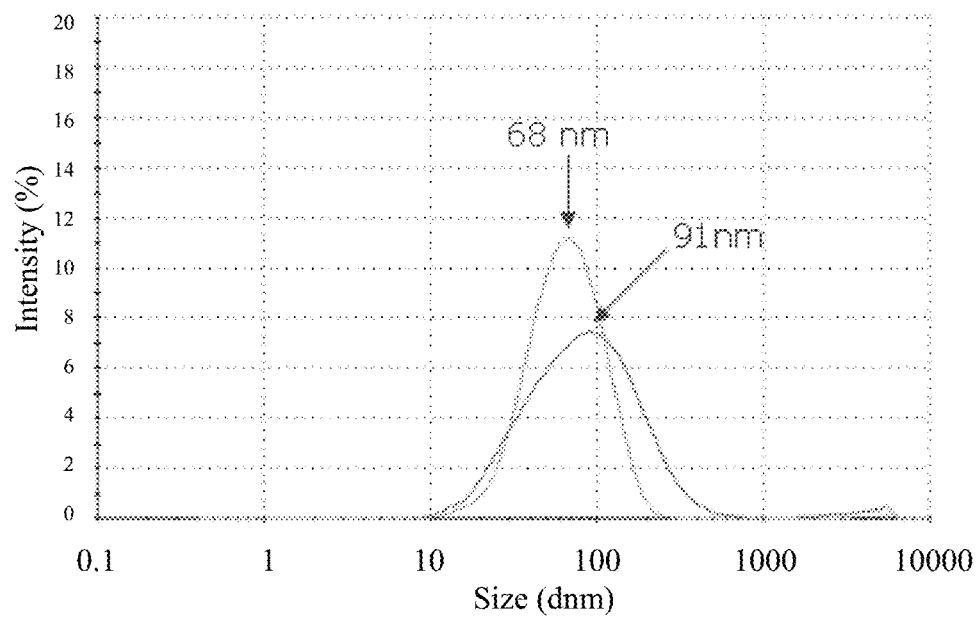
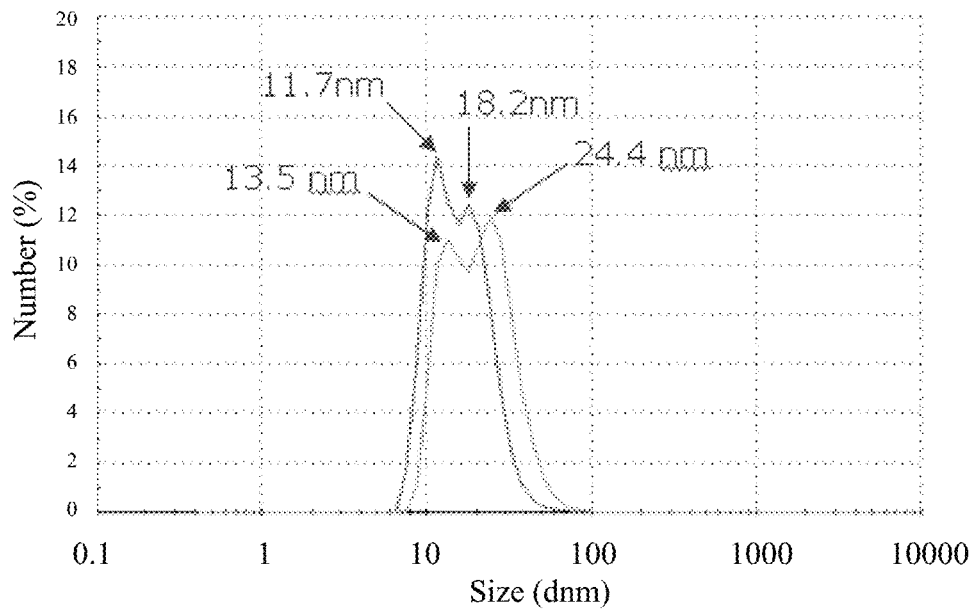

HPLC chromatogram of 4000 bar treated samples

Figure 18A

SDS Page Analysis of KSAC protein by process A

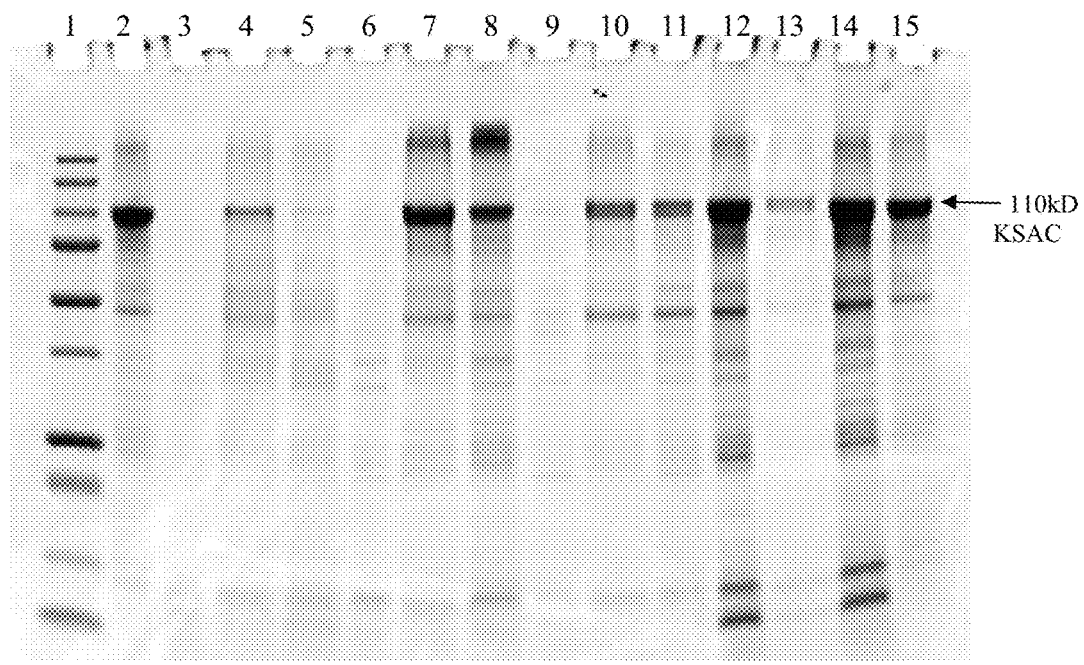

Lane 1: marker
Lane 2: KSAC inclusion bodies control
Lane 3: sample 3 supernatant
Lane 4: sample 3 pellet
Lane 5: sample 3 before centrifugation
Lane 6: sample 1 supernatant
Lane 7: sample 1 pellet
Lane 8: sample 1 before centrifugation
Lane 9: sample 4 supernatant
Lane 10: sample 4 pellet
Lane 11: sample 4 before centrifugation
Lane 12: sample 2 supernatant
Lane 13: sample 2 pellet
Lane 14: sample 2 before centrifugation
Lane 15: KSAC inclusion bodies control

Figure 18B

SDS Page Analysis of KSAC protein by process B

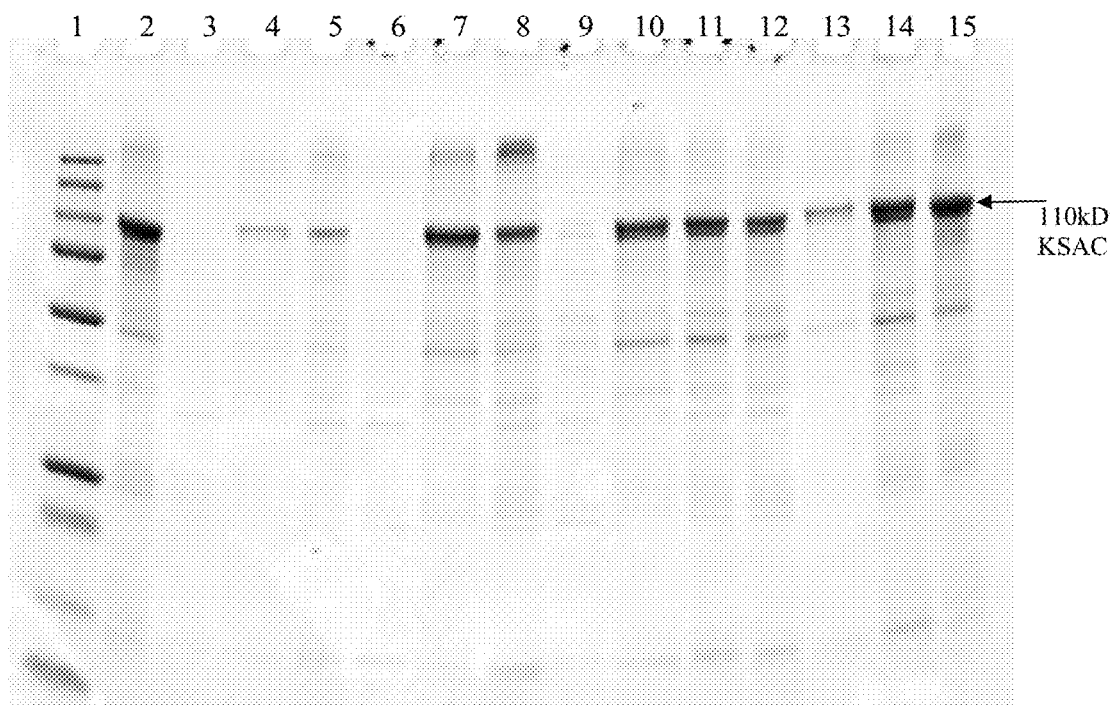

Lane 1: marker
Lane 2: KSAC inclusion bodies control
Lane 3: sample 7 supernatant
Lane 4: sample 7 pellet
Lane 5: sample 7 before centrifugation
Lane 6: sample 5 supernatant
Lane 7: sample 5 pellet
Lane 8: sample 5 before centrifugation
Lane 9: sample 8 supernatant
Lane 10: sample 8 pellet
Lane 11: sample 8 before centrifugation
Lane 12: sample 6 supernatant
Lane 13: sample 6 pellet
Lane 14: sample 6 before centrifugation
Lane 15: KSAC inclusion bodies control QDot Blott analysis of KSAC protein by process A 1: KSAC reference
2: process A without DTT (sample 1)
3: control without DTT (sample 3)
4: process A with DTT (sample 2)
5: control with DTT (sample 4)
6: 20 mM Tris buffer QDot Blott analysis of KSAC protein by process B 1: KSAC reference
2: process B without DTT (sample 5)
3: control without DTT (sample 7)
4: process B with DTT (sample 6)
5: control with DTT (sample 8)
6: 20 mM Tris buffer KSAC protein quantification from QDot Blott KSAC protein quantification from QDot Blott HPLC analysis HPLC analysis HPLC analysis

EXPRESSION OF CHIMERIC KSAC PROTEIN AND METHOD OF PRODUCING SOLUBLE PROTEINS BY HIGH PRESSURE

CROSS-REFERENCE TO RELATED APPLICATIONS

This application is a continuation of U.S. application Ser. No. 14/014,437 filed on Aug. 30, 2013, now U.S. Pat. No. 9,315,553, which claims benefit of U.S. provisional application Ser. No. 61/694,968 filed Aug. 30, 2012, and U.S. provisional application Ser. No. 61/830,425 filed Jun. 3, 2013.

FIELD OF THE INVENTION

The present invention relates to formulations for combating Leishmania infections in animals or humans. Specifically, the present invention provides pharmaceutical compositions comprising a chimeric Leishmania antigen and method of vaccination against Leishmania. The present invention also relates to methods of producing soluble or disaggregated proteins using high pressure.

BACKGROUND OF THE INVENTION

Leishmaniasis is a major and severe parasitic disease that affects humans, canines, and to a lesser degree, felines.

Leishmania and Viannia subgenera are grouped into complexes of species and subspecies based upon molecular, biochemical and immunological similarities. There are several forms of the disease named by their clinical presentation including cutaneous, mucocutaneous or visceral leishmaniasis. Each of these forms of disease is caused by different species of sand flies found in different regions of the world. Cutaneous leishmaniasis of humans is associated with members of L. aethiopica, L. major, and L. tropica complexes in the Old World and L. mexicana and L. braziliensis complexes in the New World. Visceral leishmaniasis is caused by L. donovani and L. infantum in Old World regions while L. chagasi is primarily responsible for visceral disease in the New World. Because L. infantum is the primary agent associated with canine leishmaniasis, infections in dogs often are regarded as visceral even though they tend to cause both visceral and cutaneous disease.

The agent of visceral leishmaniasis is a protozoan parasite and belongs to the leishmania donovani complex. This parasite is widely distributed in temperate and subtropical countries of Southern Europe, Africa, Asia, South America and Central America (Desjeux P. et al., 1984, Nucl. Acids Res., 12:387-395). Leishmania donovani infantum (L. infantum) is responsible for the feline and canine disease in Southern Europe, Africa, and Asia. In South America and Central America, the agent is Leishmania donovani chagasi (L. chagasi), which is closely related to L. infantum. In humans, the agent is Leishmania donovani donovani (L. donovani), which is also related to L. infantum and L. chagasi.

Leishmaniasis is a slowly progressive disease that can take up to 7 years to become clinically apparent (McConkey S E et al., 2002, Canine Vet J 43:607-609). Even then, signs are frequently nonspecific and a diagnosis of Leishmania is seldomly considered. Dogs are most commonly infected with L. infantum (L. donovani complex) which is responsible for viscerotropic disease in people. However, up to 90% of infected dogs present with both visceral and cutaneous lesions (Slappendel R J et al., 1998, In: Greene C E: Infectious Diseases of the Dog and Cat, pp 450-458). On the other hand, many dogs appear naturally resistant to this parasite and may remain asymptomatic despite known infection (Grosjean N L et al., 2002, Vet Rec 150:241-244). It is estimated that only 10% of dogs residing in endemic areas actually develop clinical disease (Lindsay D S et al., 2002, Compend Cont Educ Pract Vet 24:304-312). This lower incidence of clinical disease is attributed to a genetic predisposition of certain dogs to mount a more protective cell-mediated immune response than a humoral response (Lindsay D S et al., McConkey S E et al., Slappendel R J, et al.). Furthermore, it has been reported that up to 20% of infected dogs may mount an adequate immune response and spontaneously recover from clinical illness (McConkey S E et al.). In animals that mount a humoral response, IgG1 appears to correlate with clinical disease while asymptomatic dogs have higher IgG2 antibody levels (Lindsay et al.).

Some of the more frequently reported clinical signs of leishmaniasis include listlessness, fatigue and exercise intolerance coupled with anorexia and weight loss that eventually culminate as wasting disease (McConkey S E et al.). These signs may or may not be accompanied by fever, local or generalized lymphadenopathy (90%) and/or hepatosplenomegaly (Grosjean N L et al., 2003, J Am Vet Med Assoc 222:603-606; Lindsay D S et al., McConkey S E et al.; Martinez-Subiela S et al., 2002, Vet Rec 150:241-244). Articular involvement is also fairly common and may present as lameness with swollen joints or simply as a stiff gait. Less common findings include ocular lesions (<5%), chronic diarrhea (30%) and long, deformed brittle nails (20%) referred to as onychogryphosis (Lindsay D S et al., Slappendel R J et al.). Cutaneous lesions are present in up to 89% of infected dogs, with or without overt signs of visceral involvement. Lesions of cutaneous leishmaniasis may occur anywhere on the body but the most common sites are those which are exposed to the environment and are therefore more susceptible to bites from the sand flies. The initial papule rapidly gives rise to an ulcer. Viseral leishmaniasis is invariably fatal if not treated promptly. Viseral leishmaniasis affects the internal body organs, specifically the spleen and the liver.

Dogs are considered the major reservoir of Leishmaniasis. The disease is characterized by chronic evolution of viscerocutaneous signs occurring in less than 50% of infected animals (Lanotte G. et al., 1979, Ann. Parasitol. Hum. Comp. 54:277-95). Both asymptomatic and symptomatic dogs with detectable antibodies may be infectious (Molina R. et al., 1994, Trans. R. Soc. Med. Hyg. 88:491-3; Courtenay O. et al., 2002, J. Infect. Dis., 186:1314-20). Cats may also be carriers of the protozoan parasites and are thus considered secondary potential reservoirs.

Due to a number of factors, treatment options for leishmaniasis in dogs and response to therapy are limited at best. For some undefined reason, visceral leishmaniasis is more difficult to treat in dogs than in humans. No treatment option is 100% effective in clearing parasitic infection and clinical disease often reappears with cessation of therapy (Lindsay D S et al.). In endemic areas, the most common treatment regimen has been a combination of allopurinol with a pentavalent antimonial such as meglumine antimonite or sodium stibogluconate (Lindsay D S et al., Slappendel R J et al.). However, in recent years this protocol has fallen out of favor due to increasing resistance of the parasite to the drug as well as adverse side effects associated with these compounds (Lindsay D S et al.). To further limit treatment options, PENTOSTAM® (sodium stibogluconate) is the only available antimonial in the United States and its distribution is regulated by the Centers for Disease Control and Prevention (CDC) in Atlanta, Ga. (Lindsay D S et al.). Other investigations have sought to identify methods of preventing and treating leishmaniasis through, for example, administration of antigenic fusion polypeptides (see US 2009/0291099 which is hereby incorporated herein by reference in its entirety).

Different protocols have been tried but have proven no more efficacious at clearing parasitic infection or at preventing clinical relapse. In addition, each protocol is associated with potential adverse effects. Amphotericin B binds sterols and disrupts cell membrane permeability but is nephrotoxic (Lindsay D S et al.). When given parenterally, Paramomycin acts synergistically with antimonials causing higher levels of the antimonial for longer periods of time but is also nephrotoxic and is not currently recommended for clinical use (Lindsay D S et al.). Pentamidine isethionate is effective against leishmaniasis but requires at least 15 intramuscular injections and is quite painful (Lindsay D S et al.). Ketaconazole, miconazole, fluconazole and itraconazole are oral drugs that may be useful in containing the disease but are cost prohibitive and carry the risk of drug resistance when treating patients symptomatically. In summary, the various treatment regimens for leishmaniasis in dogs have been investigated but are not 100% efficacious; relapses are the rule rather than the exception. Ultimately, the veterinary practitioner is faced with the dilemma of treating symptomatic outbreaks of leishmaniasis in dogs at the risk of developing drug resistant strains of this parasite within the United States.

Mass detection of seropositive dogs followed by culling and/or drug treatment, or the mass application of deltamethrin-impregnated collars, was shown to have an impact in reducing human and canine Leishmaniasis prevalence in endemic areas of Southern Europe, Africa, and Asia (Maroli M. et al., 2001, Med. Vet. Entomol. 15:358-63; Mazloumi Gavgani A. S. et al., 2002, Lancet 360:374-9), although the efficacy of eliminating seropositive canines has been debated (Dietze R. et al., 1997, Clin. Infect. Dis. 25:1240-2; Moreira Jr. E. D. et al., 2004, Vet. Parasitol. 122:245-52). These control measures are either considered unacceptable, expensive or not effective (Gradoni L. et al., 2005, Vaccine 23:5245-51).

Mathematical models used to compare the effectiveness of various tools for controlling Leishmaniasis suggest that a canine vaccine may be the most practical and effective method (Dye C., 1996, Am. J. Trop. Med. Hyg. 55:125-30). Therefore, the development of vaccines able to protect canines from Leishmaniasis and/or to prevent disease progression in infected animals is highly desirable for the implementation of Leishmaniasis control programs as well for the veterinary community (Gradoni L. et al.).

Haynes et al. (Biotechnol. Prog., 2010, Vol. 26, No. 3, 743-749) discuss the use of high hydrostatic pressure to achieve high solubility and high refolding yields of growth hormone (GH) produced in E. coli inclusion bodies. U.S. Pat. Nos. 6,489,450, 7,064,192, 7,767,795 and 7,615,617 disclose reversing aggregation and increasing refolding of denatured proteins by application of high pressure.

There remains a need for effective and efficient methods of producing subunit (protein) vaccine for the treatment of Leishmania. The vaccine formulation and the method of producing such vaccine of the present invention fulfill this long felt need in the art.

SUMMARY OF THE INVENTION

The present invention demonstrated for the first time that a chimeric KSAC protein expressed in E. coli inclusion bodies was substantially solubilized and refolded after high pressure treatment.

The present invention showed surprising result that application of stepwise increase of pressure coupled with prolonged treatment of inclusion bodies under high pressure produced high yield of soluble, disaggregated, refolded and active proteins.

Compositions and vaccines comprising the chimeric KSAC protein are provided. Such vaccines or compositions can be used to vaccinate an animal and provide protection against Leishmaniasis. The KSAC protein may be expressed in E. coli inclusion bodies and is subsequently solubilized by high pressure treatment. The KSAC protein possesses immunogenic and protective properties.

Methods of the invention include methods for making and producing soluble, disaggregated, refolded or active proteins from inclusion bodies under high pressure for a prolonged period of time. Methods also include the methods of use including administering to an animal an effective amount of the antigenic KSAC protein thereof to elicit a protective immunogenic response.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIG. 1 is a table showing the SEQ ID NO assigned to each DNA and protein sequence.

FIGS. 2A-2C show the DNA and protein sequences.

FIG. 13 depicts the superposition of the DLS data obtained with the 3000 bar pressurized protein in the buffer without urea and the protein obtained with the classical refolding process.

FIGS. 18A and 18B depict the SDS-PAGE analysis of KSAC samples after high pressure treatments.

DETAILED DESCRIPTION OF THE INVENTION

Figure 3:
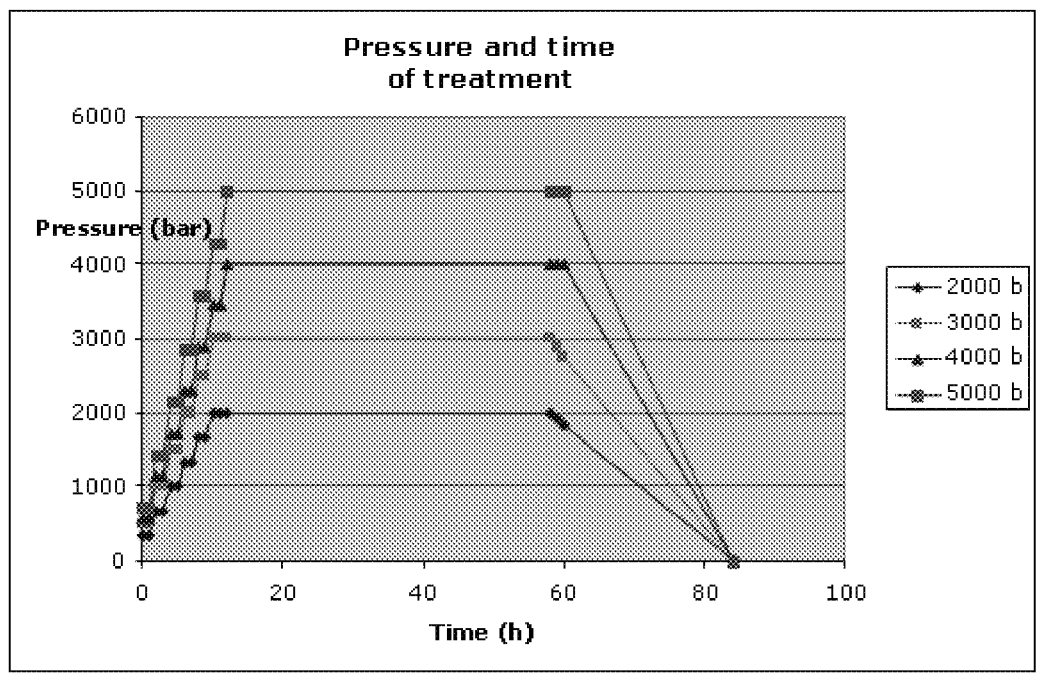
FIG. 3 is a graph representation of the pressure and time treatment of KSAC inclusion bodies.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), swine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The terms "polypeptide" and "protein" are used interchangeably herein to refer to a polymer of consecutive amino acid residues.

The terms "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA" or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers to a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "recombinant" and "genetically modified" are used interchangeably and refer to any modification, alteration or engineering of a polynucleotide or protein in its native form or structure, or any modification, alteration or engineering of a polynucleotide or protein in its native environment or surrounding. The modification, alteration or engineering of a polynucleotide or protein may include, but is not limited to, deletion of one ore more nucleotides or amino acids, deletion of an entire gene, codon-optimization of a gene, conservative substitution of amino acids, insertion of one or more heterologous polynucleotides.

The term "inclusion bodies" as used herein refers to inactive aggregates of heterologous proteins expressed in prokaryotes or eukaryotes. The terms "substantially soluble", "substantially solubilized", "substantially disaggregated" or "substantially refolded" are used interchangeably herein to refer to aggregated proteins in inclusion bodies that are at least 50%, at least 60%, at least 70%, at least 80%, at least 90%, at least 95%, or at least 98% soluble in aqueous solution, or are disaggregated, or are refolded to active form after treatments. Refolding means that a fully or partially denatured protein adopts secondary, tertiary and quaternary structure like that of the native molecule.

One embodiment of the invention provides a composition or vaccine comprising a protein produced from *E. coli*. The protein may be a fusion protein comprising two or more immunogenic portions of *Leishmania* protein selected from Kinetoplastid Membrane Protein 11 (KMP11), Sterol MethylTransferase (SMT), A2 and Cysteine Proteinase (CP). The protein may be a fusion protein comprising *Leishmania* KMP11, SMT, A2 and CP designated as chimeric KSAC protein. In one aspect of the embodiment, the KSAC protein is solubilized from the *E. coli* inclusion bodies by a high pressure. In another aspect, the KSAC protein is substantially soluble in an aqueous solution or substantially refolded.

Moreover, homologs of aforementioned proteins or polynucleotides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the polynucleotide or polypeptide sequences described above, and will exhibit a similar function.

In one embodiment, the chimeric KSAC protein has at least 70%, 75%, 80%, 85%, 90%, 95%, 96%, 97%, 98% or 99% sequence identity to a polypeptide having the sequence as set forth in SEQ ID NO:2. In another embodiment, the polynucleotide encoding the chimeric KSAC protein has at least 70%, 75%, 80%, 85%, 90%, 95%, 96%, 97%, 98% or 99% sequence identity to a polypeptide having the sequence as set forth in SEQ ID NO:2. In yet another embodiment, the KSAC encoding polynucleotide has at least 70%, 75%, 80%, 85%, 90%, 95%, 96%, 97%, 98% or 99% sequence identity to a polynucleotide having the sequence as set forth in SEQ ID NO:1.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for KSAC polypeptides, the DNA sequence of the KSAC protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of KSAC protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the KSAC polypeptide encoded by the nucleotide sequence is functionally unchanged.

In another embodiment, the present invention provides a method for producing a soluble, disaggregated, refolded or active protein expressed in prokaryotes or eukaryotes comprising the steps of (i) preparing the inclusion bodies in a buffer containing no or low concentration of urea to form inclusion body suspension; and (ii) subjecting the inclusion body suspension to a high pressure for a period of time.

In yet another embodiment, the present invention provides a method of producing a soluble, disaggregated, refolded or active protein expressed in prokaryotes or eukaryotes comprising the steps of (i) preparing the inclusion bodies in a buffer containing no or low concentration of urea to form inclusion body suspension; (ii) subjecting the inclusion body suspension to a gradual increase of pressure over a period of time; and (iii) maintaining the high pressure applied to the inclusion bodies for a period of time.

In one aspect of the embodiment, the buffer may contain DiThio Threitol (DTT). In another aspect, the DTT concentration may range from about 1 mM to about 100 mM, about 1 mM to about 90 mM, about 1 mM to about 70 mM, about 1 mM to about 60 mM, about 1 mM to about 50 mM, or about 1 mM, 2 mM, 3 mM, 4 mM, 5 mM, 6 mM, 7 mM, 8 mM, 9 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM.

In one aspect, urea may not be present in the buffer. In another aspect, urea may be present in the buffer at the concentration of about 1M, about 2M, about 3M, about 4M, about 5M, about 6M, about 7M, about 8M, about 9 M, and about 10M.

In another aspect of the embodiment, the high pressure may be in the range from about 1000 bar to about 5000 bar, from about 2000 bar to about 4000 bar. The high pressure may be any pressure in the range from about 2000 bar to about 4000 bar, for example, but not limiting to, 2000 bar, 2100 bar, 2200 bar, 2300 bar, 2400 bar, 2500 bar, 2600 bar, 2700 bar, 2800 bar, 2900 bar, 3000 bar, 3100 bar, 3200 bar, 3300 bar, 3400 bar, 3500 bar, 3600 bar, 3700 bar, 3800 bar, 3900 bar, and 4000 bar.

In another aspect of the embodiment, the gradual increase of the pressure may be done continuously or stepwise. In one aspect, the gradual increase of the pressure is applied to the inclusion body suspension by continuously increasing the pressure at a constant rate over a period of time to reach the desired final high pressure. For example, the pressure is increased at the rate of about 200 bar/min-about 1000 bar/min continuously over about 2 min-about 10 min to reach 2000 bar, at the rate of about 200 bar/min-about 1000 bar/min continuously over about 3 min-about 15 min to reach 3000 bar, at the rate of about 200 bar/min-about 1000 bar/min continuously over about 4 min-about 20 min to reach 4000 bar, at the rate of about 200 bar/min-about 1000 bar/min continuously over about 5 min-about 25 min to reach 5000 bar. In another aspect, the gradual increase of the pressure is applied stepwise. For example, the pressure is increased at about 1000 bar/min for about one minute to reach 1000 bar, then the 1000 bar pressure is maintained for about one hour to relax the protein, after the relaxation period, the pressure is increased again at about 1000 bar/min for about one minute to reach the final desired high pressure of 2000 bar. The pressure may also be increased at about 1000 bar/min for about thirty seconds to reach 500 bar, the 500 bar pressure is maintained for about one hour to relax the protein, then the pressure is increased again at about 1000 bar/min for about thirty seconds to reach 1000 bar, the 1000 bar pressure is maintained for about one hour to relax the protein, the pressure is increased again at about 1000 bar/min for about thirty seconds to reach 1500 bar, the 1500 bar pressure is maintained for about one hour to relax the protein, then the pressure is increased again at about 1000 bar/min to reach the final desired pressure of 2000 bar. To reach the final desired high pressure of 3000 bar, 4000 bar, and 5000 bar, the same stepwise increase of the pressure at about 1000 bar/min for about one minute or about 30 seconds with intermediate relaxation of protein for about one hour may be employed. For example, to reach the target pressure of 3000 bar, the pressure is increased at about 1000 bar/min for about one minute to reach 1000 bar, then the 1000 bar pressure is maintained for about one hour to relax the protein, the pressure is increased again at about 1000 bar/min for about one minute to reach the pressure of 2000 bar, then the 2000 bar pressure is maintained for about one hour to relax the protein for the second time, the pressure is increased again at about 1000 bar/min for about one minute to reach the final desired pressure of 3000 bar. To reach the target pressure of 3000 bar, the pressure can also be increased at about 1000 bar/min for about thirty seconds, with a plateau of 1 hour duration at each 500 bar, and the target pressure of 3000 bar may be reached after 5 hr. To reach the final desired pressure of 4000 bar, the pressure is increased at about 1000 bar/min for about one minute to reach 1000 bar, then the 1000 bar pressure is maintained for about one hour to relax the protein, the pressure is increased again at about 1000 bar/min for about one minute to reach the pressure of 2000 bar, then the 2000 bar pressure is maintained for about one hour to relax the protein for the second time, the pressure is increased again at about 1000 bar/min for about one minute to reach the final desired pressure of 3000 bar, then the 3000 bar pressure is maintained for about one hour to relax the protein for the third time, the pressure is increased again at 1000 bar/min for about one minute to reach the final desired pressure of 4000 bar. To reach the target pressure of 4000 bar, the pressure can also be increased at about 1000 bar/min for about thirty seconds, with a plateau of 1 hour duration at each 500 bar, and the target pressure of 4000 bar may be reached after 7 hr.

The inclusion body suspension may be treated under the high pressure for about 10 hours to about 100 hours, about 20 hours to about 100 hours. The high pressure treatment is preferably for more than 24 hours, for example, for about 25 hours to about 100 hours, about 25 hours to about 80 hours, about 25 hours to about 60 hours, about 25 hours to about 50 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 49 hours, about 50 hours.

In another embodiment, the present invention provides a method for producing a soluble, disaggregated, refolded or active protein expressed in prokaryotes or eukaryotes comprising the steps of (i) preparing the inclusion bodies in a buffer containing no or low concentration of urea to form inclusion body suspension; (ii) subjecting the inclusion body suspension to a gradual increase of pressure over a period of time; (iii) maintaining the high pressure applied to the inclusion bodies for a period of time; and (iv) recovering the protein by depressurization.

Depressurization may be performed at the rate of about 83 bar/hr-200 bar/hr.

The prokaryotes contemplated in the present invention may include *Avibacterium, Brucella, Escherichia coli, Haemophilus* (e.g., *Haemophilus suis*), *Salmonella* (e.g., *Salmonella enteridis, Salmonella typhimurium, Salmonella infantis*), *Shigella, Pasteurella*, and *Rimeirella*.

In prokaryotic systems, a number of expression vectors may be selected. Such vectors include, but are not limited to, the multifunctional *E. coli* cloning and expression vectors such as PBLUESCRIPT (Stratagene); piN vectors (Van Heeke & Schuster, J. Biol. Chem. 264:5503-5509 (1989)); and the like; PGEX Vectors (Promega, Madison, Wis.); In eukaryotic systems, the cell lines may be yeast (such as *Saccharomyces cerevisiae, Pichia pastoris*), baculovirus cells, mammalian cells, plant cells. The expression vectors of eukaryotic systems include, but are not limited to, pVR1020 or pVT1012 vectors (Vical Inc., San Diego, Calif.), PichiaPink Vector (Invitrogen, CA, USA), pFasBac TOPO vector (Invitrogen).

The method for producing a soluble, disaggregated, refolded or active protein expressed in prokaryotes or eukaryotes provided in the present invention may be used to solubilize any proteins. The proteins may include antibodies and insulin.

In another embodiment, the present invention provides a composition or vaccine comprising the chimeric KSAC protein aforementioned and a pharmaceutically or veterinarily acceptable carrier, excipient, vehicle or adjuvant.

The pharmaceutically or veterinarily acceptable carriers or adjuvant or vehicles or excipients are well known to the one skilled in the art. The pharmaceutically or veterinarily acceptable carrier or adjuvant or vehicle or excipients that can be used for methods of this invention include, but are not limited to, 0.9% NaCl (e.g., saline) solution or a phosphate buffer, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro), or facilitating transfection or infection and/or improve preservation of the vector (or protein). Doses and dose volumes are herein discussed in the general description and can also be determined by the skilled artisan from this disclosure read in conjunction with the knowledge in the art, without any undue experimentation.

Optionally other compounds may be added as pharmaceutically or veterinarily acceptable carriers or adjuvant or vehicles or excipients, including, but not limited to, alum; CpG oligonucleotides (ODN), in particular ODN 2006, 2007, 2059, or 2135 (Pontarollo R. A. et al., *Vet. Immunol. Immunopath*, 2002, 84: 43-59; Wernette C. M. et al., *Vet. Immunol. Immunopath*, 2002, 84: 223-236; Mutwiri G. et al., *Vet. Immunol. Immunopath*, 2003, 91: 89-103); polyA-polyU, dimethyldioctadecylammonium bromide (DDA) ("Vaccine Design The Subunit and Adjuvant Approach", edited by Michael F. Powell and Mark J. Newman, *Pharmaceutical Biotechnology*, 6: p. 03, p. 157); N,N-dioctadecyl-N',N'-bis(2-hydroxyethyl) propanediamine (such as AVRIDINE®) (Ibid, p. 148); carbomer, chitosan (see U.S. Pat. No. 5,980,912 for example).

The pharmaceutical compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In one embodiment, a solution of adjuvant, especially of carbomer (*Pharmeuropa*, vol. 8, No. 2, June 1996), is prepared in distilled water, advantageously in the presence of sodium chloride, the solution obtained being at an acidic pH. This stock solution is diluted by adding it to the desired quantity (for obtaining the desired final concentration), or a substantial part thereof, of water charged with NaCl, advantageously physiological saline (NaCl 9 g/l) all at once in several portions with concomitant or subsequent neutralization (pH 7.3 to 7.4), advantageously with NaOH. This solution at physiological pH is used for mixing with the vaccine, which may be especially stored in freeze-dried, liquid or frozen form. The polymer concentration in the final vaccine composition can be from 0.01% to 2% w/v, from 0.06 to 1% w/v, or from 0.1 to 0.6% w/v.

The subunit (protein) vaccine may be combined with adjuvants, like oil-in-water, water-in-oil-in-water emulsions based on mineral oil and/or vegetable oil and non ionic surfactants such as block copolymers, TWEEN®, SPAN®. Such emulsions are notably those described in page 147 of "Vaccine Design—The Subunit and Adjuvant Approach", Pharmaceutical Biotechnology, 1995, or TS emulsions, notably the TS6 emulsion, and LF emulsions, notably LF2 emulsion (for both TS and LF emulsions, see WO 04/024027). Other suitable adjuvants are for example vitamin E, saponins, and CARBOPOL® (Noveon; see WO 99/51269; WO 99/44633), aluminium hydroxide or aluminium phosphate ("Vaccine Design, The subunit and adjuvant approach", Pharmaceutical Biotechnology, vol. 6, 1995), biological adjuvants (i.e. C4b, notably murine C4b (Ogata R T et al.) or equine C4b, GM-CSF, notably equine GM-CSF (U.S. Pat. No. 6,645,740)), toxins (i.e. cholera toxins CTA or CTB, *Escherichia coli* heat-labile toxins LTA or LTB (Olsen C W et al.; Fingerut E et al.; Zurbriggen R et al. Peppoloni S et al.), and CpG (i.e. CpG #2395 (see Jurk M et al.), CpG #2142 (see SEQ. ID. NO: 890 in EP 1,221,955)).

Another aspect of the invention relates to a method for inducing an immunological response in an animal against one or more antigens or a protective response in an animal against one or more pathogens, which method comprises inoculating the animal at least once with the vaccine or pharmaceutical composition of the present invention. Yet another aspect of the invention relates to a method for inducing an immunological response in an animal to one or more antigens or a protective response in an animal against one or more *Leishmania* pathogens in a prime-boost administration regime, which is comprised of at least one primary administration and at least one booster administration using at least one common polypeptide, antigen, epitope or immunogen. The immunological composition or vaccine used in primary administration may be same, may be different in nature from those used as a booster. The prime-administration may comprise one or more administrations. Similarly, the boost administration may comprise one or more administrations. The prime-boost administrations may be carried out 2 to 6 weeks apart, for example, about 3 weeks apart. According to one embodiment, a semi-annual booster or an annual booster, advantageously using the subunit (protein) vaccine, is also envisioned.

The prime-boost administration can include the subunit vaccine or composition comprising the chimeric KSAC protein aforementioned. The prime-boost administration can also include recombinant viral vectors and plasmid vectors expressing *Leishmania* antigens (see, for example, US2009/0324649 which is hereby incorporated herein by reference in its entirety). In one aspect of the prime-boost regime, the composition or vaccine comprising the KSAC protein is administered followed by the administration of vaccine or composition comprising a recombinant viral vector that contains and expresses any *Leishmania* antigens, or a DNA plasmid vaccine or composition that contains and expresses any *Leishmania* antigens, or an inactivated viral vaccine or composition comprising the *Leishmania* antigens.

Usually, one administration of the vaccine is performed at 10 to 15-week old by the subcutaneous or intramuscular route. A second or third administration can be done within the 2-6 weeks of the first administration. The animals are preferably at least 4-week old at the time of the first administration.

A variety of administration routes may be used in addition to subcutaneously or intramuscularly, such as intradermally or transdermally.

The composition or vaccine according to the invention comprise or consist essentially of or consist of an effective quantity to elicit a therapeutic response of one or more polypeptides as discussed herein; and, an effective quantity can be determined from this disclosure, including the documents incorporated herein, and the knowledge in the art, without undue experimentation.

For the composition or vaccine comprising the expressed KSAC protein of the present invention, a dose may include, from about 1 µg to about 2000 µg, about 5 µg to about 1000 µg, about 10 µg to about 100 µg, about 20 µg to about 1000 µg, about 30 µg to about 500 µg, or about 50 µg to about 500 µg. The dose volumes can be between about 0.1 ml to about 10 ml, or between about 0.2 ml to about 5 ml.

The invention will now be further described by way of the following non-limiting examples.

EXAMPLES

Construction of DNA inserts, plasmids and recombinant viral or plant vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1 Solubilization of KSAC Protein Expressed in *E. coli* Inclusion Bodies The KSAC inclusion bodies produced from *E. coli* were prepared in the following three buffers: 1) Tris 20 mM, 50 mM DiThio Threitol (DTT), pH8; 2) Tris 20 mM, 50 mM DiThio Threitol (DTT), pH8, urea 1M; 3) Tris 20 mM, 50 mM DiThio Threitol (DTT), pH8, urea 2M. The KSAC inclusion bodies prepared in the same buffers at room temperature without pressure during the entire treatment duration were used as controls.

FIG. 3 shows the steps of pressure levels for protein relaxation during the pressure increase (stepwise increase of pressure). Pressurization at target pressure was applied for 48 hours, then the samples were depressurized for 24 hours.

Figure 4:
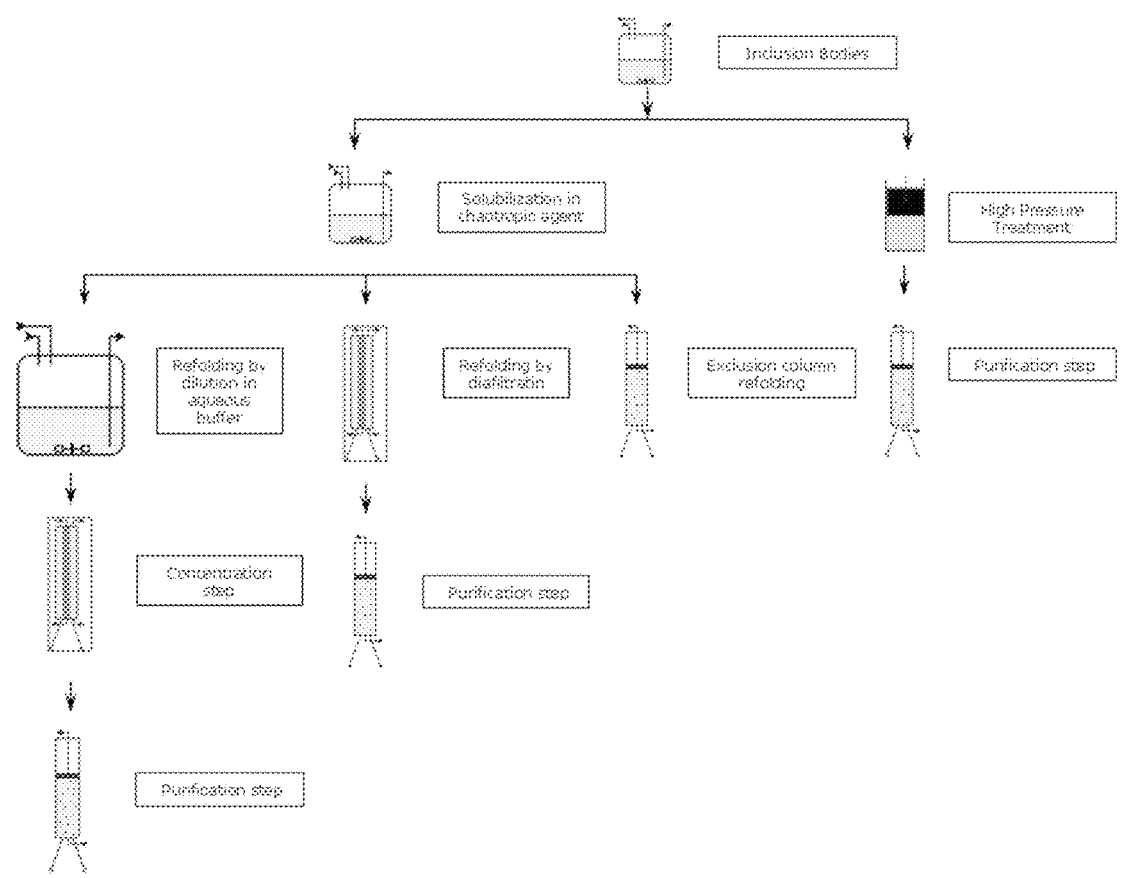
FIG. 4 is a schematic representation of comparison between high pressure treatment and classical chromatography refolding.

FIG. 4 shows the schematic comparison between the high pressure solubilisation and folding of recombinant proteins from inclusion bodies and the classical solubilisation and folding of recombinant proteins from inclusion bodies.

Figure 5:
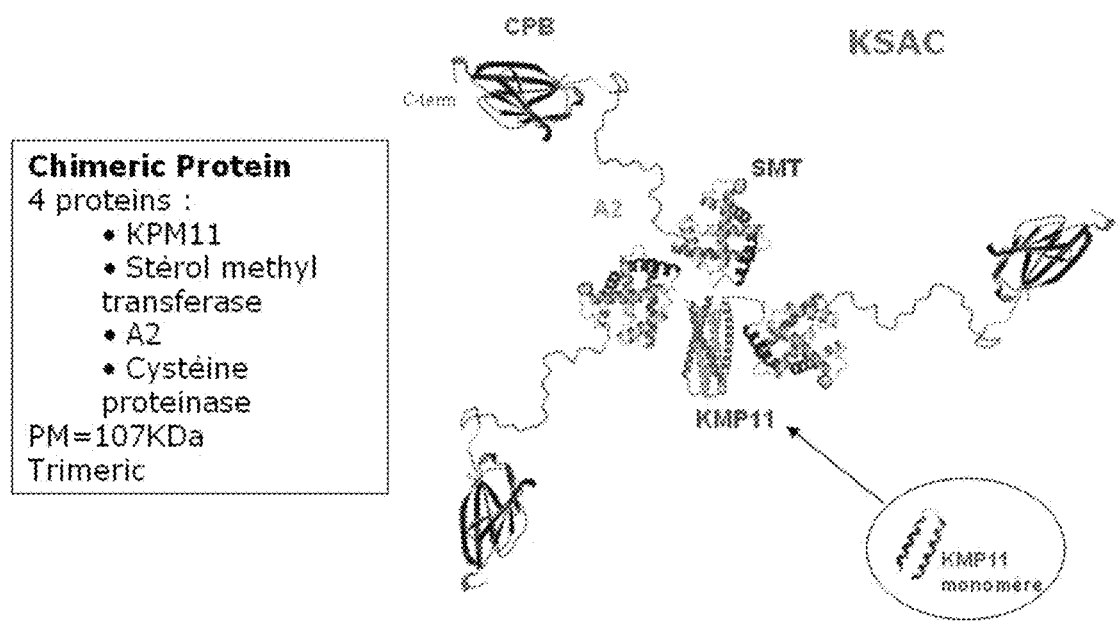
FIG. 5 is the graphic representation of KSAC refolding process.
Figure 6:
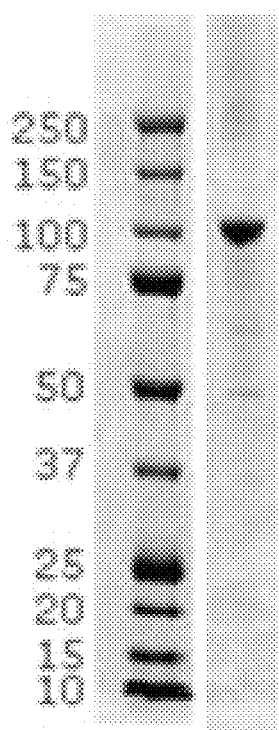
FIG. 6 depicts the SDS-PAGE of KSAC refolded by exclusion chromatography.
Figure 7:
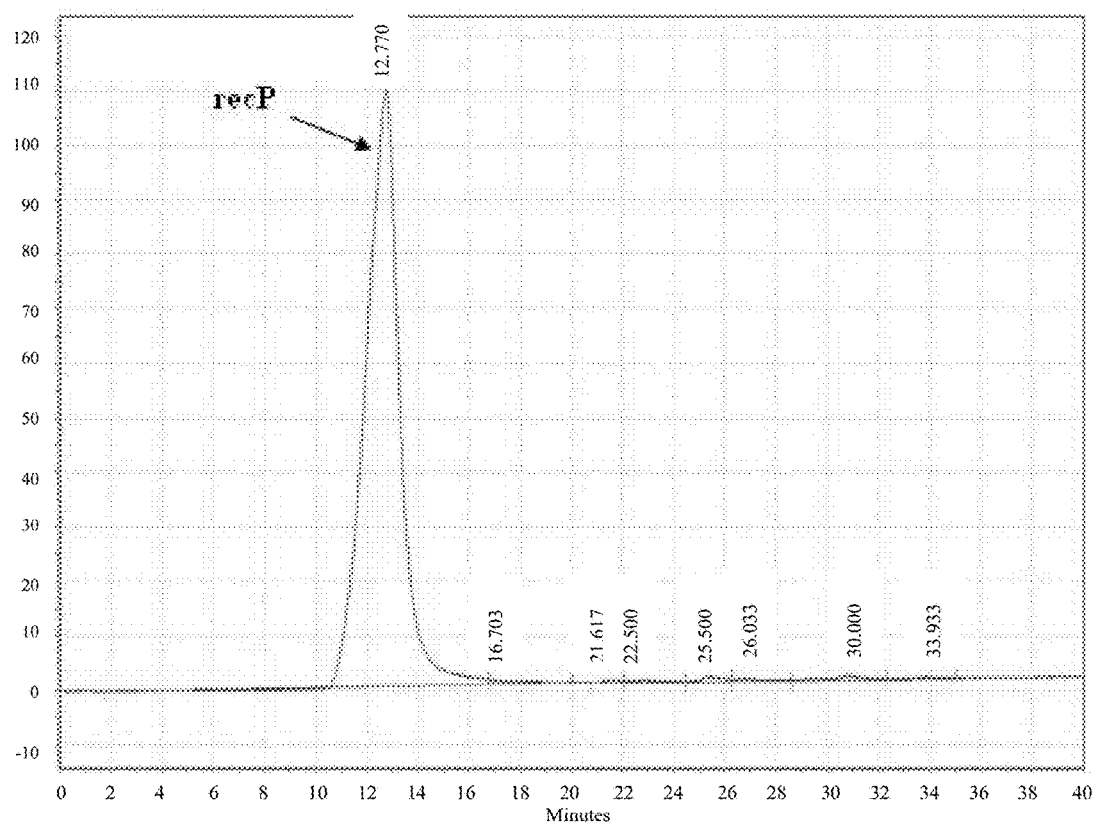
FIG. 7 depicts the HPLC plot of refolded KSAC by exclusion chromatography.
Figure 8A:
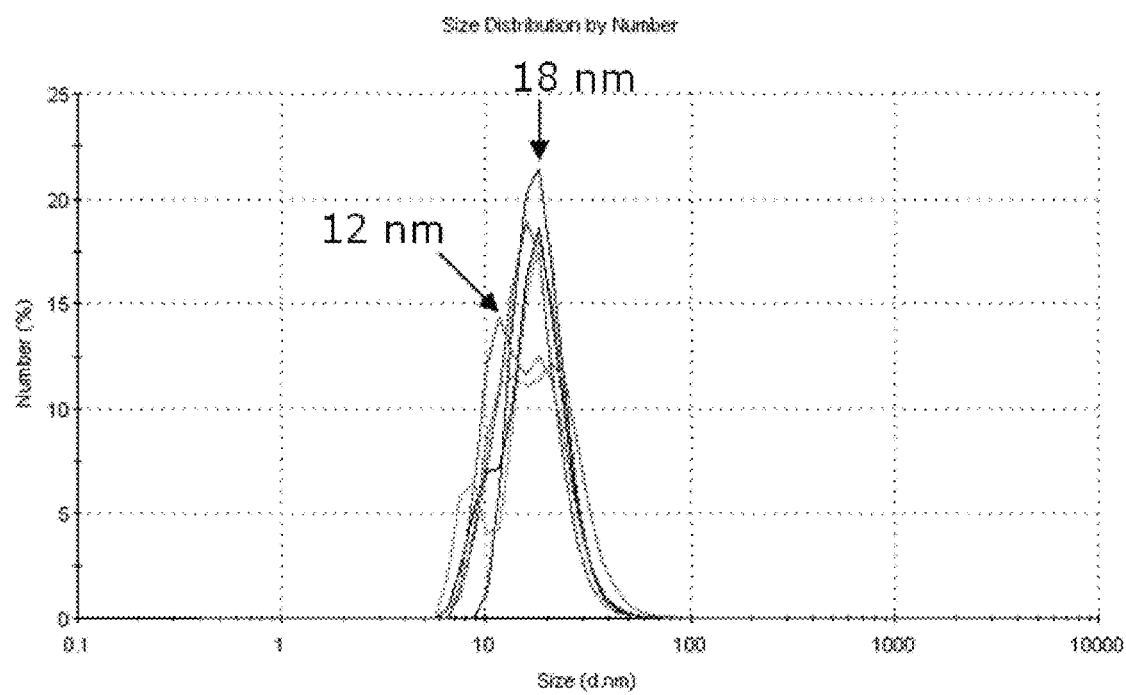
FIGS. 8A and 8B depict the dynamic light scattering (DLS) of refolded KSAC protein using exclusion chromatography.
Figure 8B:
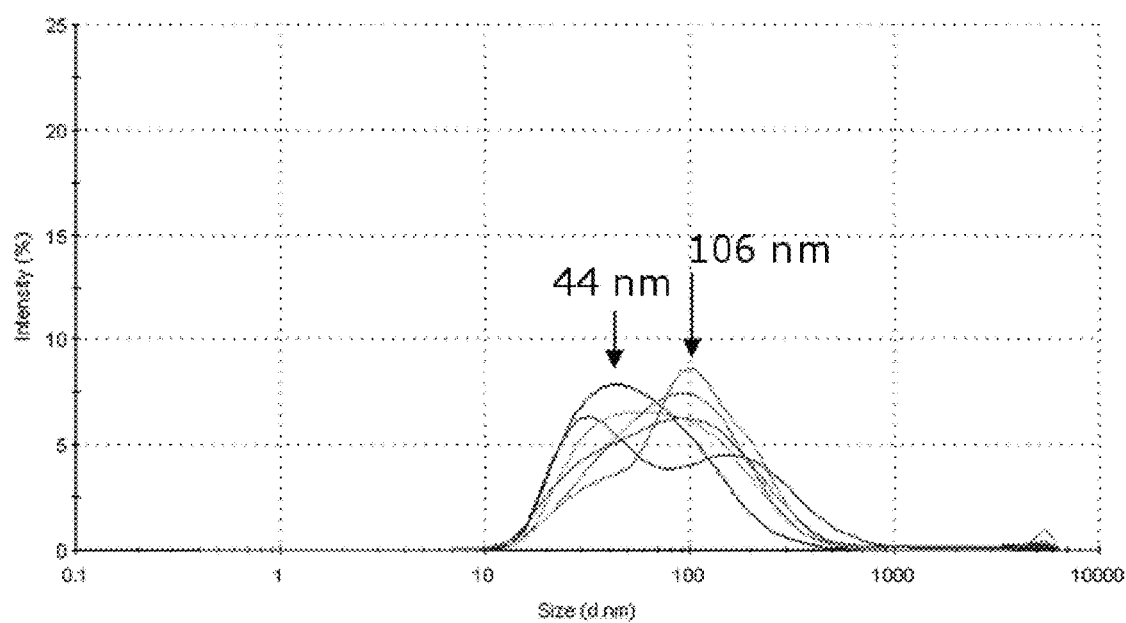

FIG. 5 shows the schematic graph of KSAC refolding. FIG. 6 shows the typical SDS-PAGE pattern of the KSAC protein after the KSAC protein was solubilized in 7M urea, 20 mM DTT and refolded by exclusion chromatography. FIG. 7 shows the typical HPLC plot of the KSAC protein. The HPLC chromatogram identifies the trimer of KSAC protein by its mass. The protein concentration and the relative purity towards total protein content were estimated. FIG. 8 shows the dynamic light scattering (DLS) of refolded KSAC protein using exclusion chromatography. FIG. 8A shows the distribution by number which indicates that the majority of the population has a size of 12 to 18 nm. FIG.

8B shows the exhaustive range of size detected that is not linked to relative population. Objects between 10 and 800 nm were detected.

Figure 9:
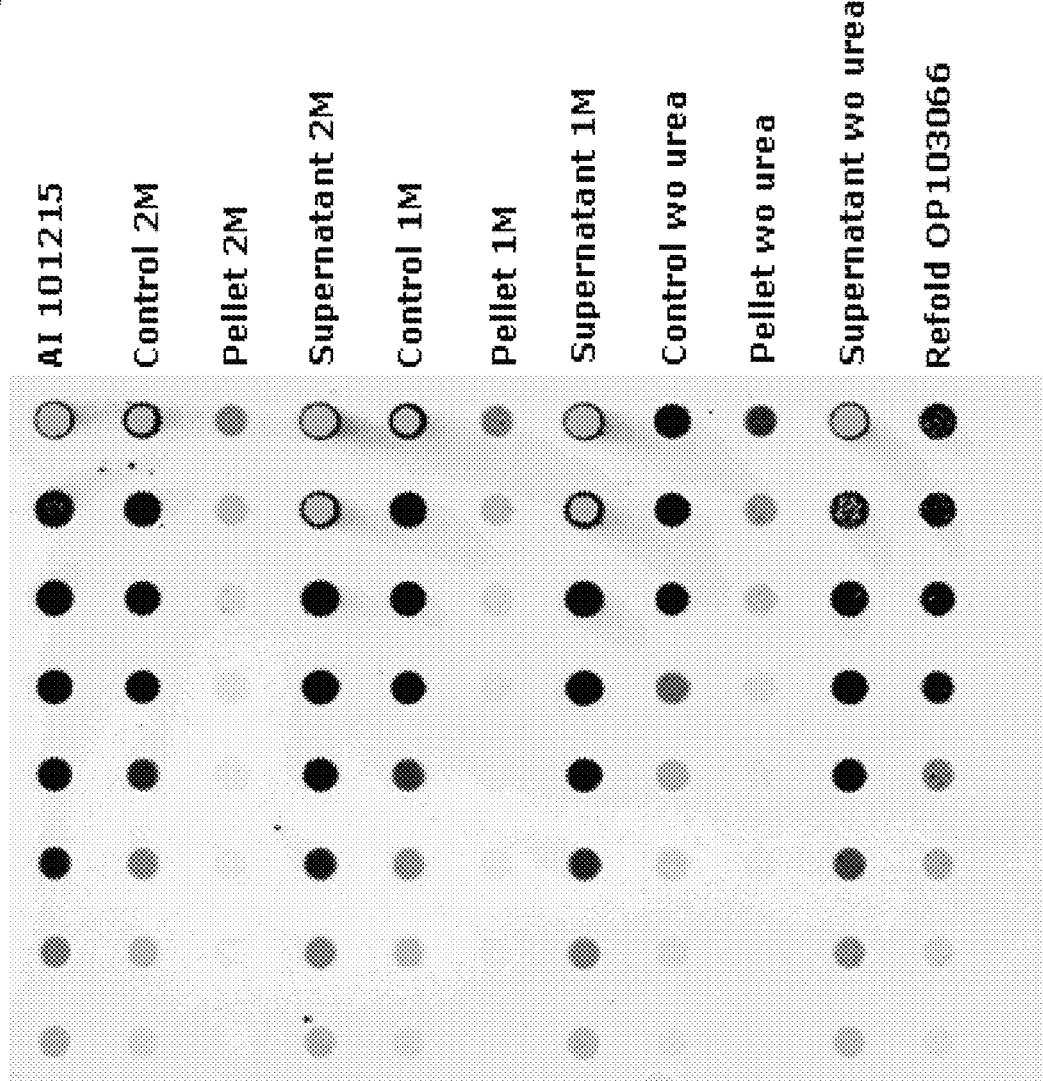
FIG. 9 depicts the Qdot-blot of KSAC samples treated with 3000 bar.
Figure 10:
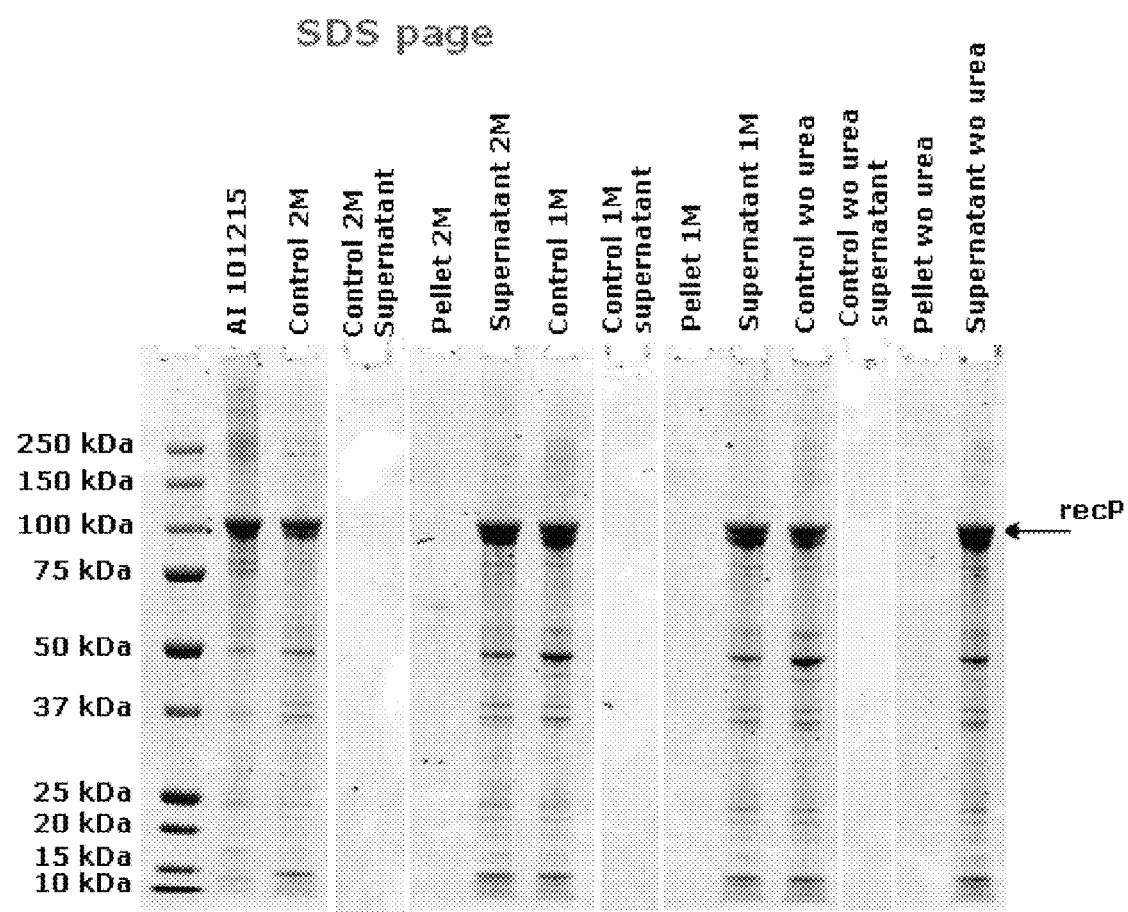
FIG. 10 depicts the SDS-PAGE of KSAC samples treated with 3000 bar.

The Qdot-blot (FIG. 9) and SDS-PAGE (FIG. 10) analysis of the inclusion bodies pressurized at 3000 bars and the control samples showed that all proteins are in the supernatant phase of the treated sample in all three buffers which indicates that the proteins are solubilized.

Figure 11:
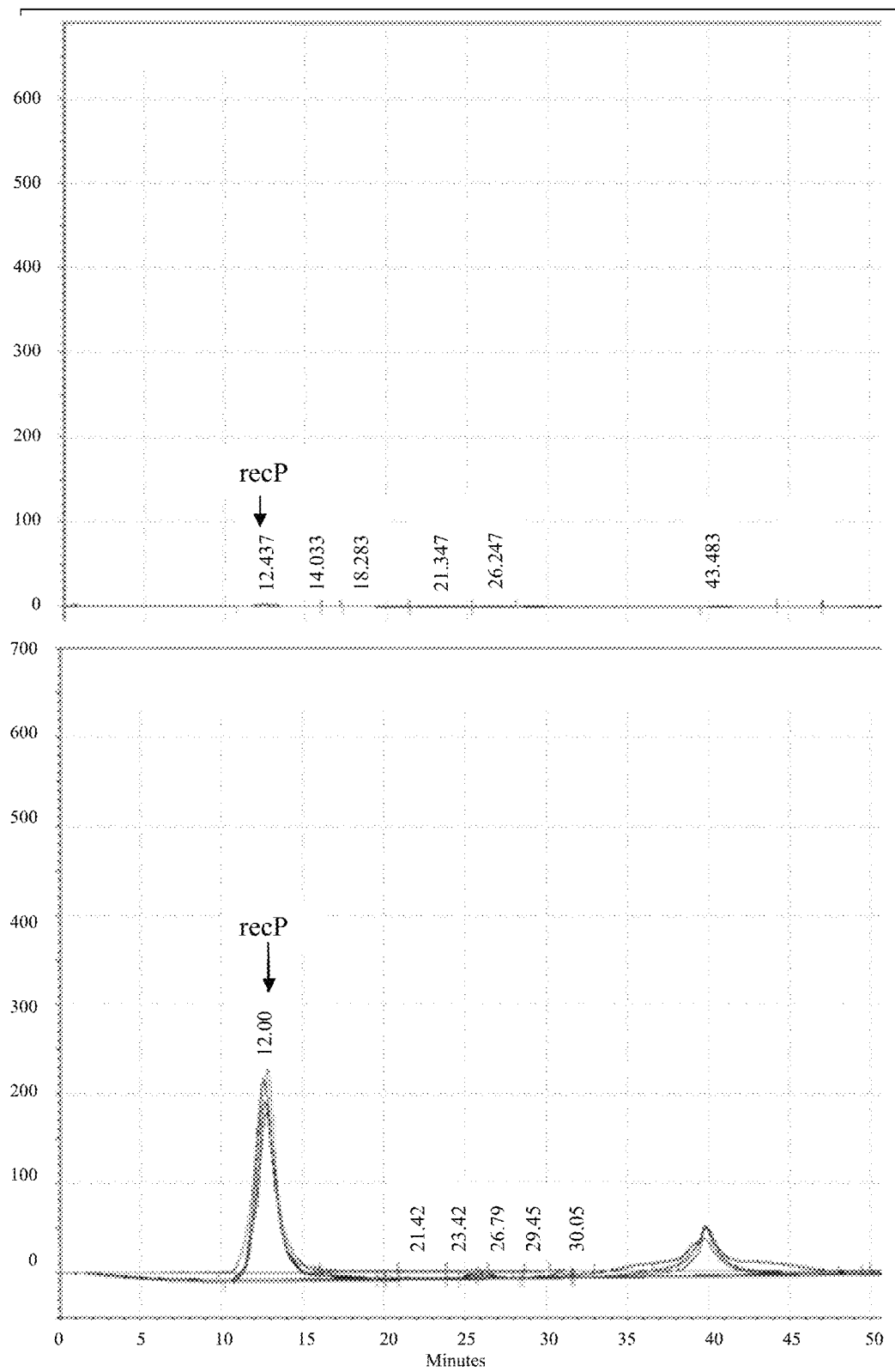
FIG. 11 depicts the HPLC of control samples and solubilized KSAC after 3000 bar treatment.

Superposition of the HPLC chromatograms of the supernatant of the controls (FIG. 11 upper panel) and all the 3000 bar treated samples (FIG. 11 lower panel) showed that no protein is detected in the controls while the KSAC protein and all the other proteins present in the inclusion bodies are detected after pressure treatment which means that all the proteins are solubilized after pressure treatment.

Figure 12:
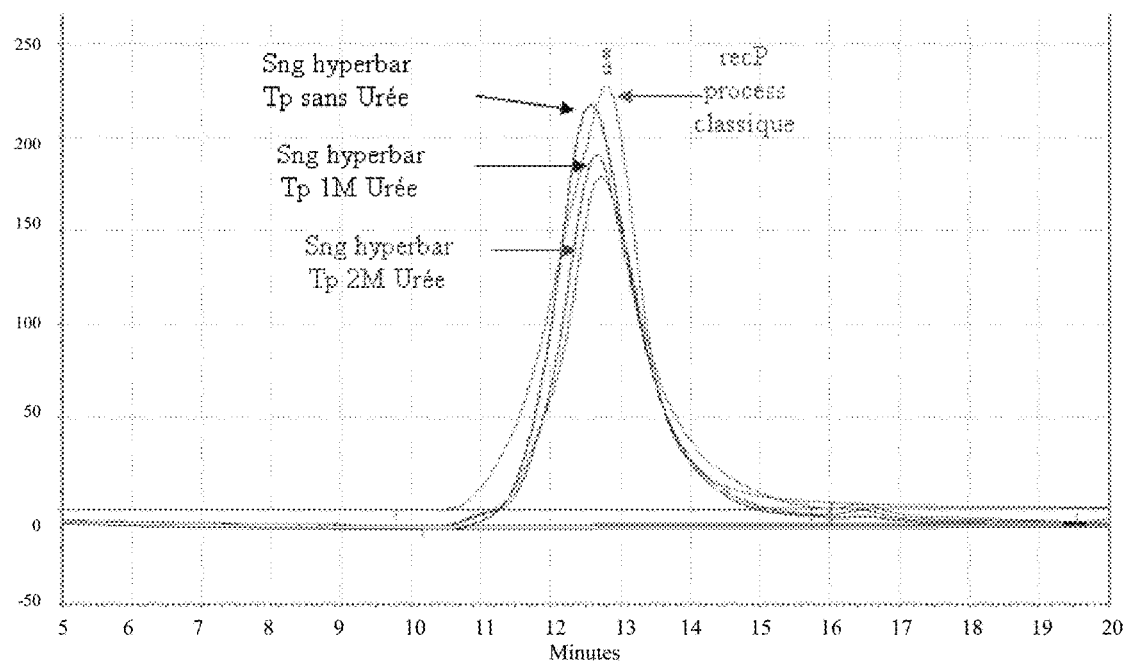
FIG. 12 depicts the superposed HPLC chromatogram of the supernatant of the 3000 bar pressure treated KSAC samples and the KSAC protein obtained with the classical refolding process.

FIG. 12 is the superposed HPLC chromatogram of the supernatant of the 3000 bar pressure treated KSAC samples and the KSAC protein obtained with the classical refolding process. The results show that the peaks are similar that the soluble protein obtained by high pressure treatment is organized in trimer.

Table 1 below shows quantification of KSAC protein after 3000 bar treatment by qDot-blot and HPLC.

TABLE 1

|  | control | Assay pellet | Assay supernatant |
|---|---|---|---|
| 2M urea | | | |
| Dot-blot µg/ml | 347 | 10 | 797 |
| HPLC µg/ml | — | — | 723 |
| 1M urea | | | |
| Dot-blot µg/ml | 328 | 10 | 750 |
| HPLC µg/ml | — | — | 746 |
| Without urea | | | |
| Dot-blot µg/ml | 123 | 15 | 649 |
| HPLC µg/ml | — | — | 825 |

The quantity of solubilized protein was about 800 µg/ml. This was very close to the estimated quantity of initial KSAC protein as inclusion bodies (1000 µg/ml). The solubilisation yield is very high (75-100%).

FIG. 13 shows the superposition of the DLS data obtained with the 3000 bar pressurized protein (lighter line) in the buffer without urea and the protein obtained with the classical refolding process (darker line). The exhaustive range of size (upper panel) shows that less objects of higher size are detected in pressurized samples. The distribution by number (lower panel) shows that the majority of the pressure-refolded population has a similar size with the population refolded by the classical process and the folding seems very similar.

Figure 14:
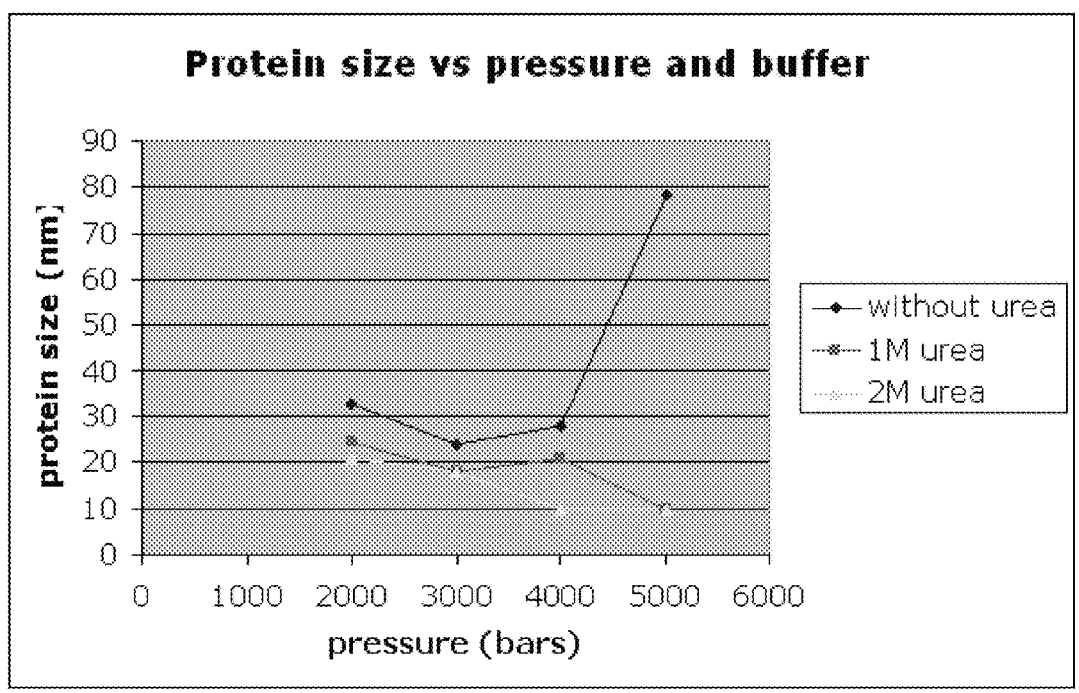
FIG. 14 shows the effect of pressure and buffer on the protein sizes.

FIG. 14 shows that the protein sizes obtained at 3000 bar are identical to protein sizes obtained from classical chromatography refolding for all three buffers used (circled). When treated at 2000 bar, the protein sizes are identical to the protein sizes from classical chromatography refolding when urea is used in the buffer. At pressure higher than 3000 bar, high-pressure aggregates appear when no urea is used. With urea present in the buffer, the protein seems to collapse (10 nm in size) which indicates that denaturation has occurred.

Figure 15A:
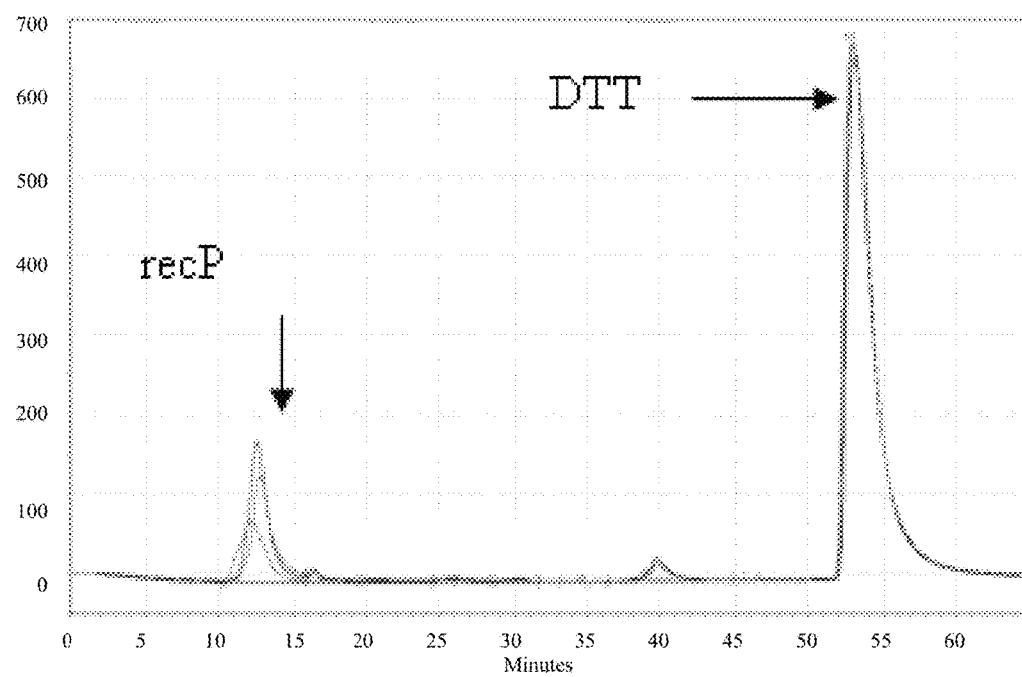
FIGS. 15A and 15B depict the HPLC chromatogram of 4000 bar treated samples.
Figure 15B:
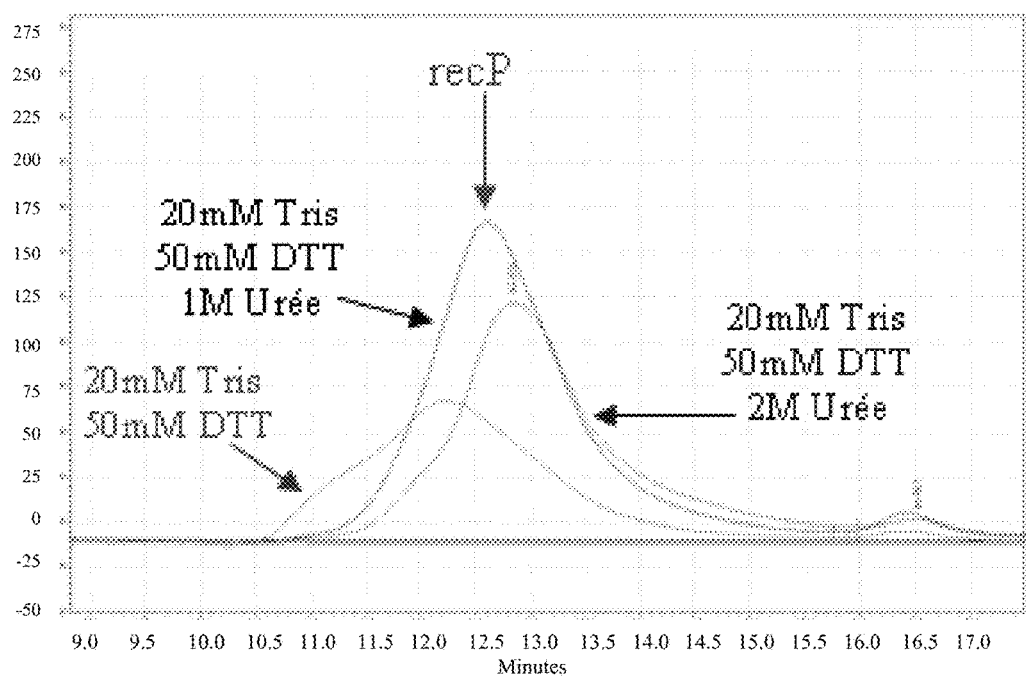

FIG. 15 shows HPLC chromatogram of 4000 bar treated samples. The results show that proteins with sizes larger than KSAC protein appeared when no urea was present in the buffer, or with only 1M urea was added in the buffer. Protein size was as expected when 2M was added in the buffer.

Figure 16:
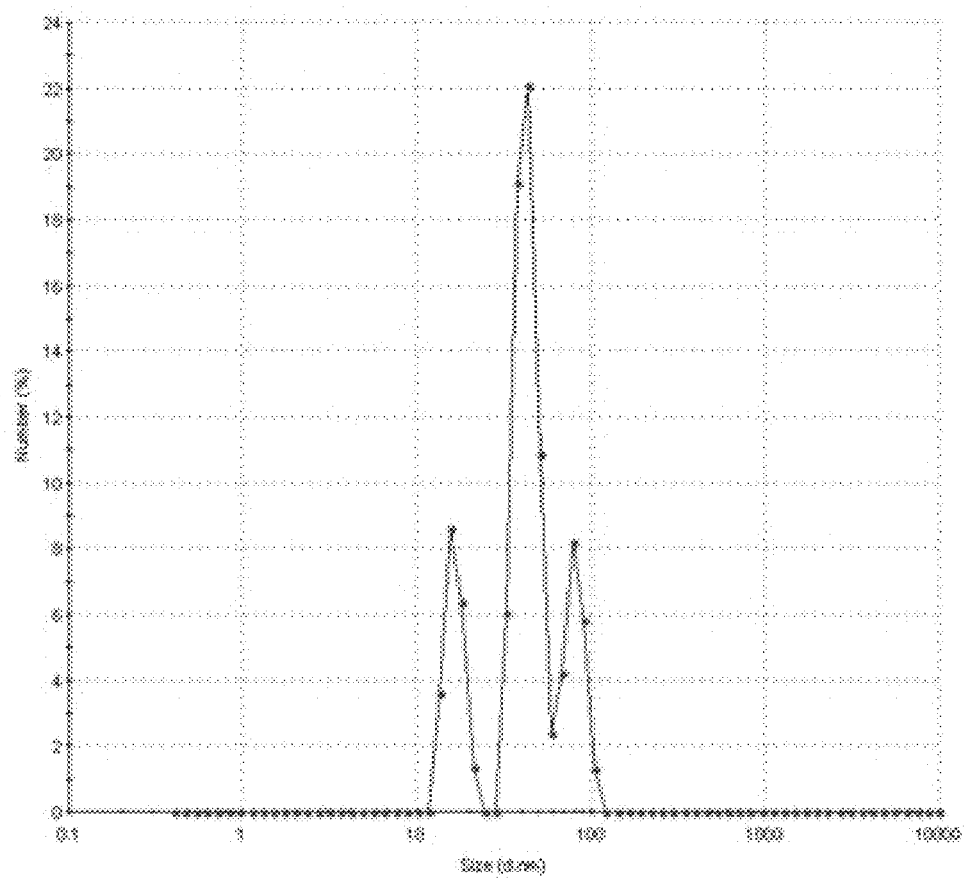
FIG. 16 shows the DLS size distribution by number of the 5000 bar treated samples without urea.

FIG. 16 shows the DLS size distribution by number of the 5000 bar treated samples without urea. The results indicate that three populations of proteins were detected with large sizes up to 90 nm. The population whose size is similar to the chromatography refolded KSAC is a minority one.

Figure 17:
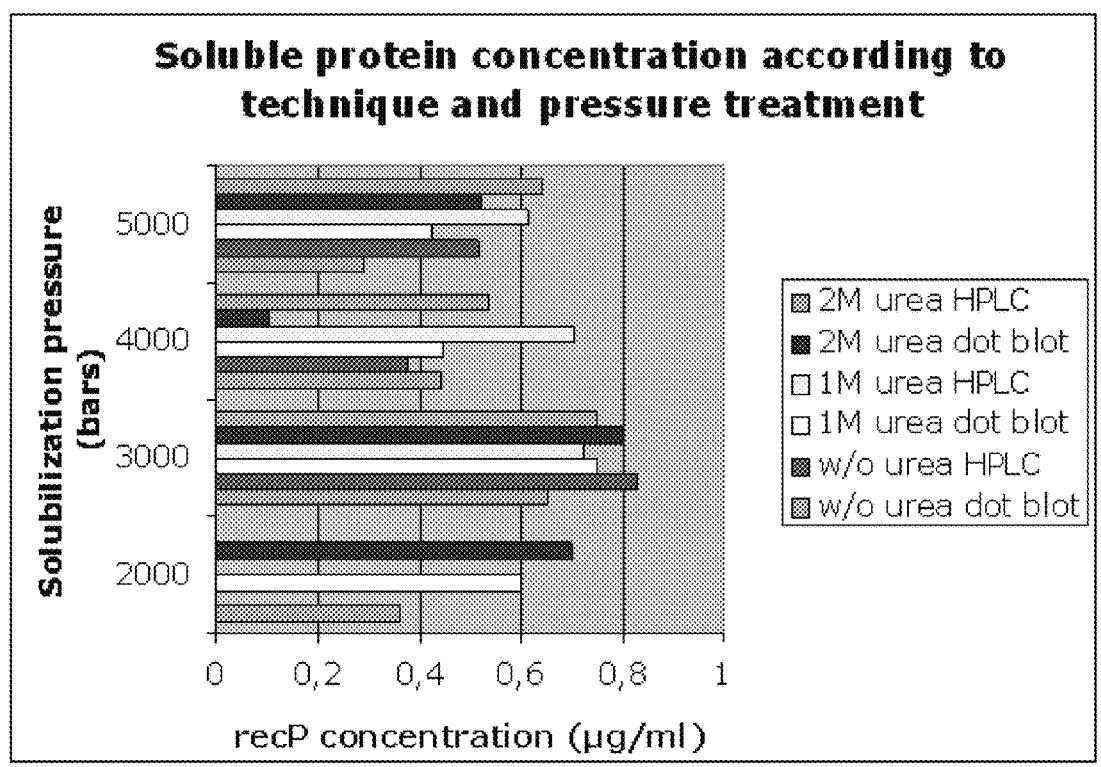
FIG. 17 shows the comparison of KSAC soluble protein content determined by HPLC and Qdot-blot.
Figure 19A:
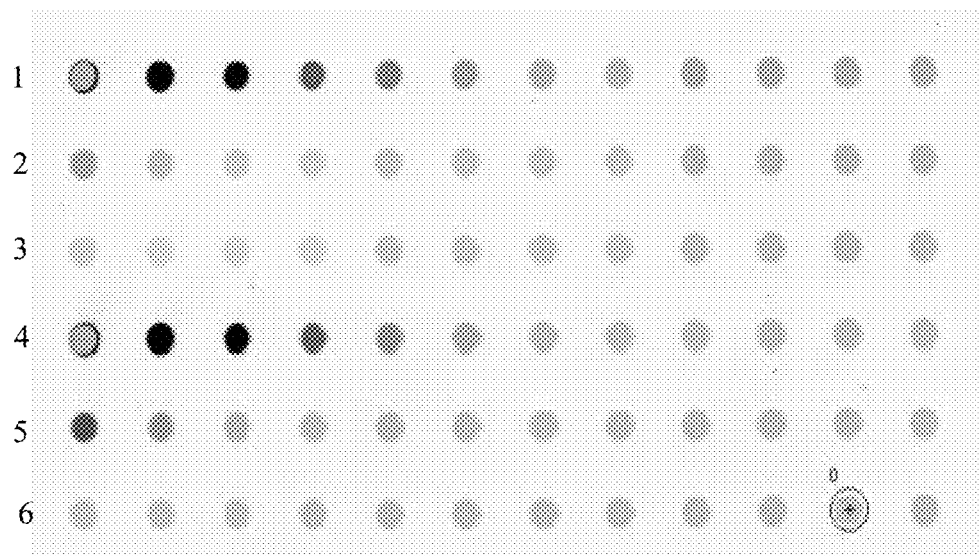
FIGS. 19A-19D depict the Q-Dot Blott analysis of KSAC samples after high pressure treatments.
Figure 19B:
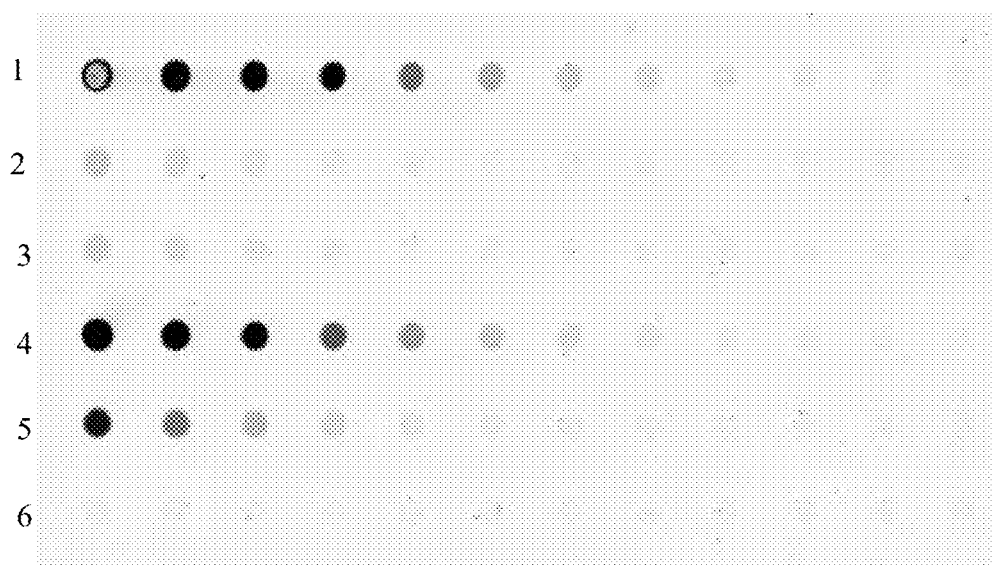
Figure 19C:
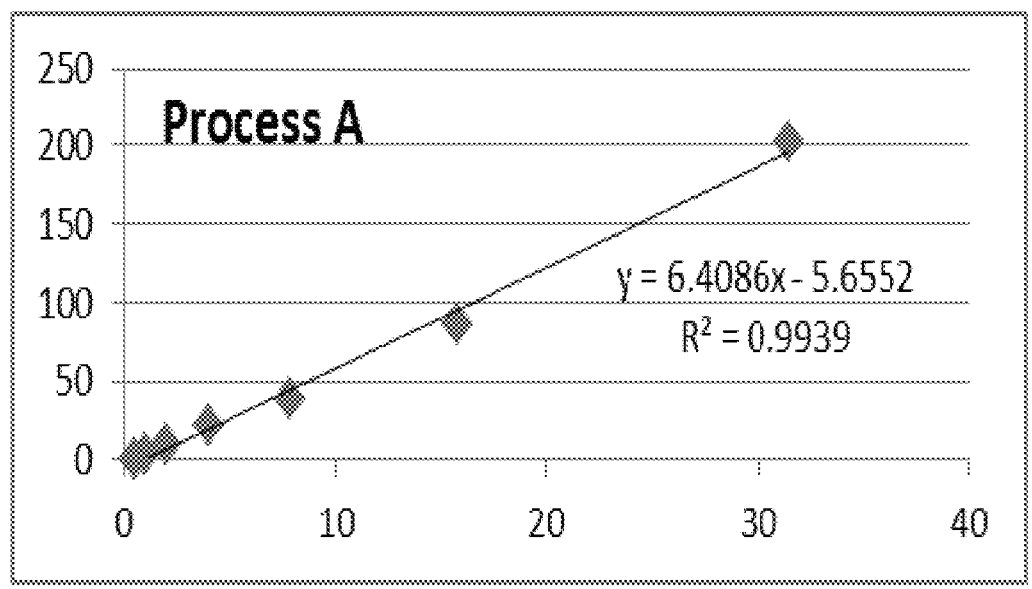
Figure 19D:
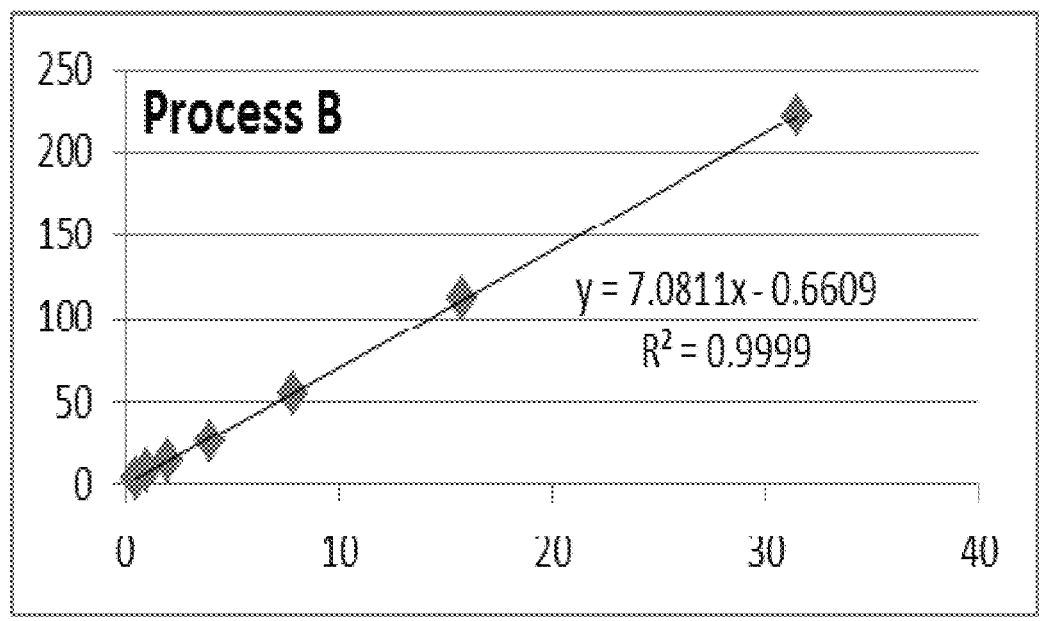

FIG. 17 shows the comparison of KSAC soluble protein content determined by HPLC and Qdot-blot. The results indicate that the maximum concentrations of solubilized proteins are obtained with 3000 bar treated samples with good consistency between HPLC and Qdot-blot technologies. For the 2000 bar treated samples, the presence of urea helps to increase the solubilization yield. For the 4000 bar treated samples, HPLC gives higher yield than Qdot-blot, indicating a loss of recognition of the antigens.

Example 2 Vaccination of Dogs Using KSAC Vaccine

In this study, forty-nine 15-week old beagle dogs were vaccinated according to the following protocol.

TABLE 2

| Group | Vaccination 1 ml (10 µg) SC at D 0, D 21, D 42 and M 12 (booster) | Post vaccinal survey*** | Blood sampling for immunological survey |
|---|---|---|---|
| Vaccinated (n = 24) | KSAC*/ GLA-SE** | D 0 + 4/6 h, D 1, D 2 | D 0, D 28, D 35, D 50, D 56 |
| Controls (n = 25) | Placebo | D 21 + 4/6 h, D 22 and D 23 D 42 + 4/6 h, D 43 and D 44 M 12 + 1 day and + 3 days | |

*KSAC: purified KSAC protein in Tris buffer (20 mM, pH = 8), 10 µg/ml
**GLA-SE: oil-in-water emulsion (4% oil)
***post vaccinal survey was performed as long as any sign was detected After vaccination (on D77), the dogs were transferred to South Italy, in a highly endemic area for canine Leishmaniasis to testing up to 15 months (M15). Post vaccinal survey included the evaluation of rectal temperature, general condition (see Table 3), pain on palpation (presence/absence), cutaneous heat (presence/absence), itching (presence/absence) and swelling. Swellings were scored as follow; 0=no swelling, 1=minor swelling (only detectable), 2=swelling but <2 cm, 3=swelling >2 cm.

The post vaccinal survey showed that no major sign (persisting pain, important itching) was detected during the observation period.

TABLE 3

Clinical signs evaluated during canine Leishmaniasis survey and calculation of the Overall Clinical Score (OCS)

| Clinical signs | Measurement | Scoring |
|---|---|---|
| Body condition (See Annex 3) | Moderate, Stout or Obese | 0 |
| | Thin | 1 |
| | Emaciated | 3 |
| General condition | Good = animal in good health which plays and is attentive | 0 |
| | Apathy = animal with lack of energy (when compared to its normal behaviour) or animal which stays lying but responds to stimuli | 1 |
| | Depression = animal which stays lying without responding to stimuli | 3 |

TABLE 3-continued

Clinical signs evaluated during canine Leishmaniasis survey
and calculation of the Overall Clinical Score (OCS)

| Clinical signs | Measurement | Scoring |
|---|---|---|
| Cutaneous signs | Absence | 0 |
|  | Bilateral symetric alopecia | 1 |
|  | Ulcers/Nodules | 2 |
|  | Exfoliative dermatitis | 3 |
| Ocular signs | Absence | 0 |
|  | Blepharitis and/or conjunctivitis and/or keratitis | 1 |
|  | Uveitis | 2 |
| Epistaxis | Absence | 0 |
|  | Presence | 3 |
| Arthritis | Absence | 0 |
|  | Presence | 1 |
| Lymph node and/or spleen enlargement | Absence | 0 |
|  | Bilateral enlargment of lymph nodes prescapular or retromandibular lymph nodes and of popliteal Lymph nodes- 3 And/or Spleen enlargment- 3 | 3 |

For each category, only the highest score was considered in the calculation of the Overall Clinical Score (OCS). The scores of the seven categories are summed to determine the OCS.

The OCS data indicated that no major abnormality of the OCS was detected before M15.

Infection patterns were categorized into 4 categories (Oliva et al. 2006, J of Clin Microbiol 44:1318-22) and regrouped in non-established (alias non active) and active infections depending on whether culture-based analysis was positive or negative.

TABLE 4

Terminology used for the classification of the dogs according
to their parasitological, serological and clinical signs

|  | Healthy | PCR negative |
|---|---|---|
|  |  | Cult negative |
|  |  | Sero negative |
| Non established infection | Sub-patent | PCR positive |
|  |  | Cult negative |
|  |  | Sero negative or positive |
| Active infection | Asymptomatic | PCR positive |
|  |  | Cult positive |
|  |  | Sero positive |
|  |  | Healthy |

TABLE 4-continued

Terminology used for the classification of the dogs according
to their parasitological, serological and clinical signs

|  | Symptomatic | PCR positive |
|---|---|---|
|  |  | Cult positive |
|  |  | Sero positive |
|  |  | Clinical and/or biological sign(s) |

PCR = qPCR on spleen aspirate
Cult = Culture on Lymph node aspirate or LDA on spleen aspirate
Sero = serology by IFAT
Clinical and/or biological sign(s) = non null OCS The parasitological and serological assays were performed to evaluate the status of the dogs as defined by Oliva et al (2006). Nested PCR on bone marrow, culture on lymph nodes aspirates were performed according to Gradoni et al (2005, Vaccine 23:5245-5251). IFAT (ImmunoFluorescent Antibody Test) serum titers test was performed according to a technique derived from OIE (2004, Manual of diagnostic tests and vaccines for terrestrial animals, fifth Edition OIE, Paris). Quantitative PCR and LDA (Limiting Dilution Assay) on spleen aspirate were performed using methods derived from Bretagne et al (2001, Clin Diagn Lab Immunol 8:828-831) and Hill et al. (1983, Infect Immun 39:1087-1094), respectively.

TABLE 5

Results of culture on Lymph nodes aspirates and
LDA performed on specimens collected at M 8,
M 12 and M 15 indicating active infections

|  | M 8 | | M 12 | | M 15 | |
|---|---|---|---|---|---|---|
|  | Culture LN | LDA spleen | Culture LN | LDA spleen | Culture LN | LDA spleen |
| Vaccinated group (24 dogs) | | | | | | |
| Neg | 23 | 21 (2 NT*) | 23 | 22 | 21 | 22 |
| Pos | 1 | 1 | 1 | 2 | 3 | 2 |
| Control group (25 dogs) | | | | | | |
| Neg | 24 | 24 | 23 | 19 | 16 | 15 |
| Pos | 1 | 1 | 3 | 6 | 9 | 10 |

*NT: not tested

TABLE 6

Results of serological (IFAT) and parasitological assays (nPCR
on Bone Marrow aspirates and quantitative PCR on spleens aspirates)
performed on specimens collected at M 8, M 12 and M 15

|  | M 8 | | | M 12 | | | M 15 | | |
|---|---|---|---|---|---|---|---|---|---|
|  | IFAT | nPCR BM | Q-PCR spleen | IFAT | nPCR BM | Q-PCR spleen | IFAT | nPCR BM | Q-PCR spleen |
| Vaccinated group (24 dogs) | | | | | | | | | |
| Neg | 23 | 23 | 33 (1 NT) | 21 | 21 | 21 | 20 | 16 | 21 |
| Pos | 1 | 1 | 1 | 3 | 3 | 3 | 4 | 8 | 3 |

TABLE 6-continued

Results of serological (IFAT) and parasitological assays (nPCR on Bone Marrow aspirates and quantitative PCR on spleens aspirates) performed on specimens collected at M 8, M 12 and M 15

| | M 8 | | | M 12 | | | M 15 | | |
|---|---|---|---|---|---|---|---|---|---|
| | IFAT | nPCR BM | Q-PCR spleen | IFAT | nPCR BM | Q-PCR spleen | IFAT | nPCR BM | Q-PCR spleen |
| Control group (25 dogs) | | | | | | | | | |
| Neg | 24 | 24 | 23 | 21 | 15 | 17 | 28 | 10 | 15 |
| Pos | 1 | 1 | 2 | 4 | 10 | 8 | 7 | 15 | 10 |

In addition to the tests done in Table 6, IFAT titers were also measured on samples collected at M0 (time corresponding to the peak of vaccine induced antibody response) on both vaccinated and control dogs, and all samples were found negative.

TABLE 7

Repartition of the dogs according to classes defined in Table 4

| | | M 8 | | M 12 | | M 15 | |
|---|---|---|---|---|---|---|---|
| | | Con* | Vac** | Con* | Vac** | Con* | Vac** |
| Non established infection | Healthy | 23 | 23 | 16 | 21 | 15 | 21 |
| | Sub-patent | 1 | 0 | 3 | 1 | 0 | 0 |
| Active infection | Asymptomatic | 1 | 1 | 6 | 2 | 8 | 1 |
| | Symptomatic | 0 | 0 | 0 | 0 | 2 | 2 |

Con*: Controls
Vac**: Vaccinated

The results indicated a high proportion of dogs with active infections among control dogs (at M15, 40%, 10/25) and a lower proportion of dogs with active infections among vaccinated dogs (at M15, 12.5%, 3/24).

The study shows that after 15 months in the endemic area, a reduction of the proportion of dogs with active *Leishmania* infected was observed in vaccinated versus control dogs (i.e. vaccine efficacy). The vaccine efficacy was evaluated at 69%. These results are consistent with a significant control of parasite infection in vaccinated dogs.

The result also demonstrated that vaccination with the subunit KSAC vaccine does not interfere with the IFAT serology test. This supports the possibility to vaccinate in endemic areas without interfering with on-going epidemiology studies and clinical assessment of the dogs.

Example 3 Comparison of Different Processes of Solubilizing KSAC Protein

The objective of the study is to compare the efficiency of solubilizing protein from inclusions bodies by different processes.

The KSAC inclusion bodies produced from *E. coli* were prepared in the following buffers to form inclusion bodies suspension: a) 20 mM Tris buffer, 50 mM DiThioThreitol (DTT), pH=8.0; b) 20 mM Tris buffer, pH=8.0.

The inclusion bodies suspensions were stored in Quick Seal tubes for high pressure treatments as described below.

In process A, stepwise pressurization was applied to the inclusion bodies suspensions increasing the pressure from 0 bar to 3000 bar at 1000 bar/min, with a plateau of 1 hour duration at each 500 bar (target pressure of 3000 bar reached after 5 hr). The 3000 bar pressure was maintained for 48 hours. The samples were then depressurized from 3000 bar to 0 bar at constant rate of 125 bar/hr for 24 hrs.

In process B, the inclusions bodies suspensions were treated according to the method described in U.S. Pat. No. 6,489,450. The samples were subject to pressurization at constant rate up to 2500 bar in 1 hr. The 2500 bar pressure was maintained for 6 hrs. Depressurization was performed at constant rate for 1 hr reducing the pressure from 2500 bar to 0 bar.

Samples were prepared as shown in Table 8 below.

TABLE 8

| | inclusion bodies suspensions treatment | |
|---|---|---|
| Sample (1 mg/mL KSAC inclusion bodies) | buffer | High pressure treatment process |
| 1 | Tris 20 mM | Process A |
| 2 | Tris 20 mM + DTT 50 mM | Process A |
| 3 | Tris 20 mM | Control* |
| 4 | Tris 20 mM + DTT 50 mM | Control |
| 5 | Tris 20 mM | Process B |
| 6 | Tris 20 mM + DTT 50 mM | Process B |
| 7 | Tris 20 mM | Control |
| 8 | Tris 20 mM + DTT 50 mM | Control |

Control*: no high pressure treatment, stored at room temperature.

SDS-PAGE Analysis

After the high pressure treatments, the samples were centrifuged to separate the supernatant and pellets, and processed for protein analysis on SDS-PAGE. The SDS-PAGE analysis is shown in FIGS. 18A and 18B. Each well was loaded with either 5 μl of sample (crude), 5 μl of supernatant, 5 μl of pellet resuspended in Tris buffer.

The KSAC protein amounts calculated from the band intensity on the SDS-PAGE were presented in Table 9 below.

TABLE 9

Comparative integration of the intensities of the bands measured on SDS gels

| | | Process A | | | | Process B | | | |
|---|---|---|---|---|---|---|---|---|---|
| sample | | I.I. KSAC band | Total protein I.I. | % KSAC/ total | % KSAC-S/% KSAC-P* | I.I. KSAC band | Total protein I.I. | % KSAC/ total | % KSAC-S/% KSAC-P |
| KSAC reference | | 36 | 49 | 73% | | 29 | 47 | 62% | |
| Control - no DTT | S[1] | 0 | 0 | 0% | — | 0 | 0 | 0% | — |
| | P[2] | 13 | 26 | 50% | | 4 | 5 | 80% | |
| | C[3] | 3 | 21 | 14% | | 6 | 16 | 38% | |
| Process - no DTT | S | 0 | 9 | 0% | 0% | 0 | 2 | 0% | 0% |
| | P | 43 | 76 | 57% | | 28 | 39 | 72% | |
| | C | 27 | 86 | 31% | | 14 | 41 | 34% | |
| Control - with DTT | S | 1 | 8 | 13% | — | 0 | 0 | 0% | — |
| | P | 20 | 40 | 50% | | 24 | 36 | 67% | |
| | C | 16 | 31 | 52% | | 22 | 37 | 59% | |
| Process - with DTT | S | 55 | 127 | 43% | 75% | 18 | 29 | 62% | 69% |
| | P | 8 | 14 | 57% | | 8 | 9 | 89% | |
| | C | 45 | 106 | 42% | | 28 | 47 | 60% | |
| KSAC reference | | 38 | 52 | 73% | | 29 | 45 | 64% | |

S[1]: supernatant
P[2]: pellet
C[3]: crude, before centrifugation
% KSAC-S/% KSAC-P*: [% KSAC/total in supernatant]/[% KSAC/total in pellet]

The results show that there is no significant amount of KSAC detected in the supernatant of the controls or the samples treated with processes A and B when buffer containing no DTT was used. Soluble KSAC protein was found in the supernatant of the samples treated with high pressure (both processes A and B) when buffer containing DTT was used. Surprisingly, the results of protein quantification from SAS-PAGE also indicate that process A provided better solubilization when compared to process B. This surprising result was further confirmed by the more accurate calculation of the solubilization yield for each high pressure process using Q-Dot Blott and HPLC.

Q-Dot Blot Analysis

The supernatants of the samples were analyzed by Q-Dot Blott to estimate the amount of KSAC protein solubilized by the treatments. The results are shown in FIGS. 19A-19D and Table 10.

TABLE 10

Concentrations of solubilized KSAC found in the supernatants for controls and high pressure processed samples

| Identification | Process A | Process B |
|---|---|---|
| Treatment without DTT | 26.0 g/ml | 12.7 g/ml |
| Control without DTT | 0 | 9.9 g/ml |
| Treatment with DTT | 632.1 g/ml | 368.9 g/ml |
| Control with DTT | 61.7 g/ml | 63.9 g/ml |

No significant difference was observed between the control samples (no high pressure treatment) with and without DTT. There was no soluble KSAC found in the supernatant. The Q-Dot Blott result confirmed the SDS-PAGE result.

The treatment performed using process A with DTT allowed solubilizing and refolding of the KSAC protein (detected by Q-Dot Blott). The concentration of soluble KSAC protein was found to be 632 µg/mL using process A while concentration of KSAC protein obtained using the process B was only about 369 g/mL. The solubilization yields obtained are 63% for process A and 37% for process B. The Q-Dot Blott results further demonstrate that process A is more efficient in producing soluble and refolded proteins.

HPLC Analysis

Figure 20:
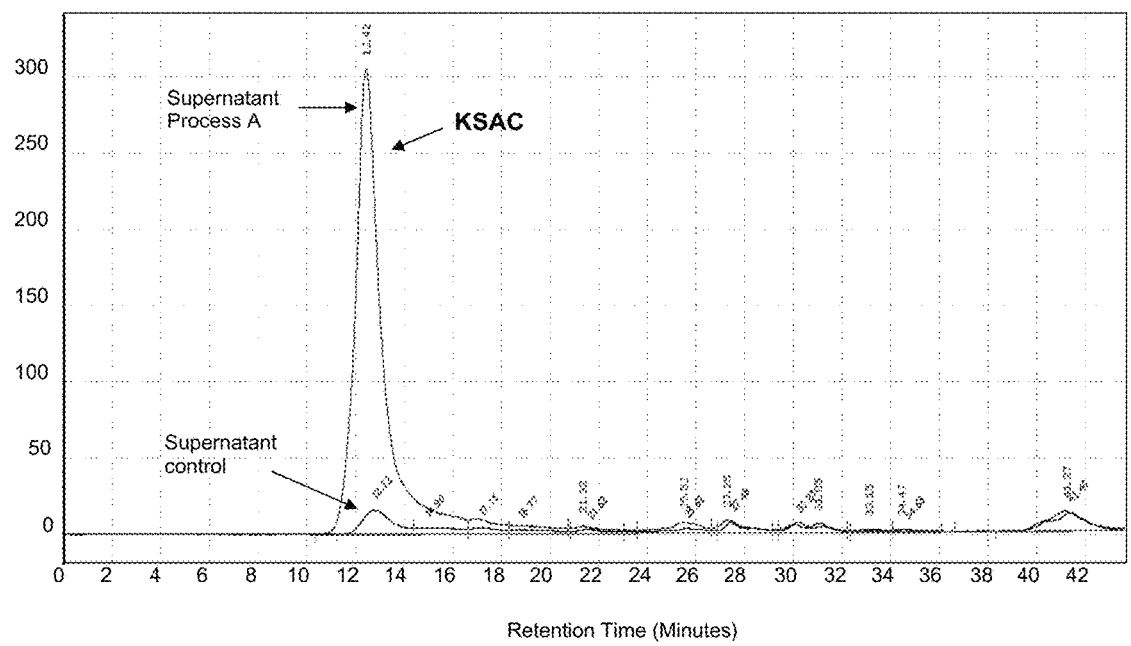
FIG. 20 depicts the HPLC analysis of KSAC samples after process A treatment.

FIG. 20 shows the superposition of the HPLC chromatograms of the supernatant of the control and process A treated sample. The retention time, retention volume and estimated purity obtained for the process A treated sample are show in Table 11 below.

TABLE 11

Retention time, retention volume and estimated purity obtained for process A treated sample

| Detection | Information | Control - no processing | After Process A |
|---|---|---|---|
| UV | RT (Retention time - min) | 12.7 | 12.4 |
| | VR (Retention volume - mL) | 6.64 | 6.46 |
| | Estimated Purity (%) | 17.3 | 85.5 |

Figure 21:
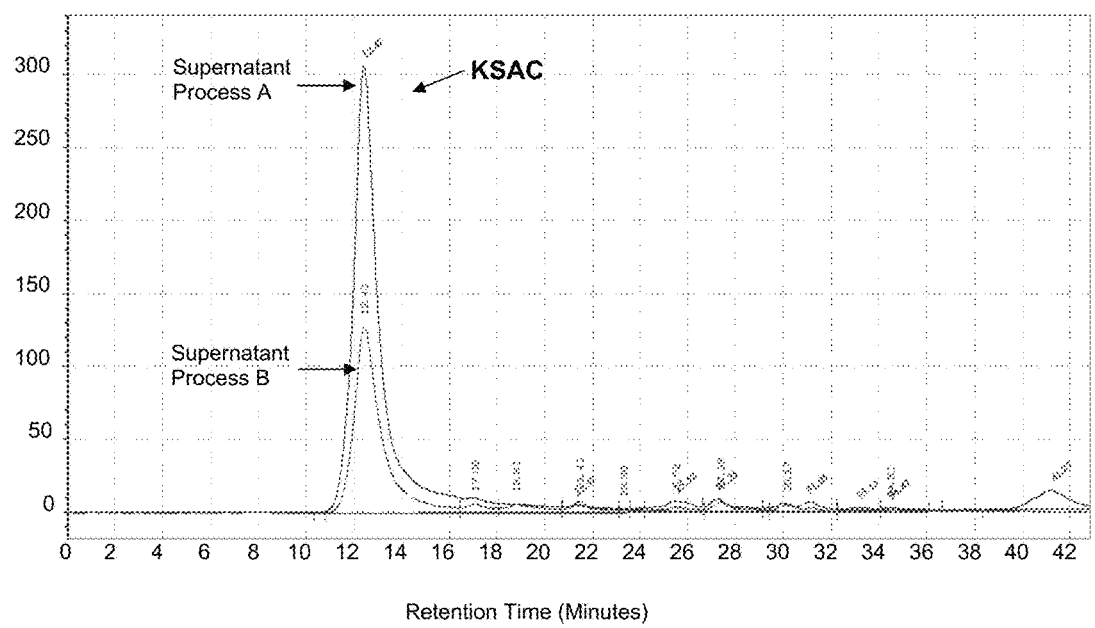
FIG. 21 depicts the HPLC analysis of KSAC samples after process B treatment.

FIG. 21 shows the superposition of the HPLC chromatograms of the supernatant of process A treated sample and process B treated sample. The retention time, retention volume and estimated purity obtained for the process A treated sample are show in Table 12 below.

TABLE 12

Retention time, retention volume and estimated purity obtained for process A and B treated samples

| Detection | Information | Process A | Process B |
|---|---|---|---|
| UV | RT (Retention time - min) | 12.4 | 12.4 |
| | VR (Retention volume - mL) | 6.46 | 6.47 |
| | Estimated Purity (%) | 85.5 | 74.2 |

Figure 22:
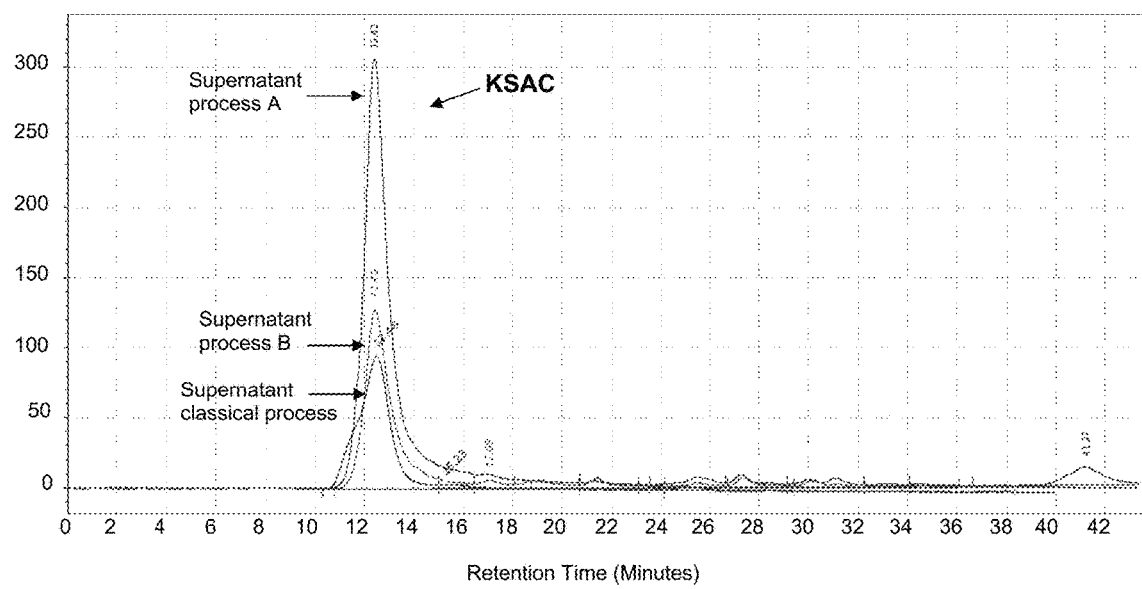
FIG. 22 depicts the HPLC analysis of KSAC samples after process A, process B and classical process treatments.

FIG. 22 shows the superposition of the HPLC chromatograms of the supernatant of process A treated sample, process B treated sample and classical process treated sample (denaturation and refolding obtained by urea and DTT treatment). The retention time, retention volume and estimated purity obtained for the process A treated sample are show in Table 13 below.

TABLE 13

Retention time, retention volume and estimated purity obtained for process A, process B and classical process treated samples

| Detection | Information | Classical process | Process A | Process B |
|---|---|---|---|---|
| UV | RT (Retention time - min) | 12.5 | 12.4 | 12.4 |
|  | VR (Retention volume - mL) | 6.50 | 6.46 | 6.47 |
|  | Peak area (mAU) | 8628 | 25251 | 10506 |
|  | Estimated purity (%) | 94.7 | 85.5 | 74.2 |

The HPLC results further confirmed that process A provided better solubilization of KSAC protein than process B judging from the peak areas (25251 mAU for process A vs 10506 mAU for process B). Both process A and B allow obtaining a refolding of the KSAC protein very close to the one obtained using the classical process (solubilization using urea+DTT treatment and refolding by SEC chromatography).

The trials performed with both processes A and B did not yield significant soluble KSAC protein in the absence of DTT. The results confirmed that a reducing agent is needed during the high pressure treatment to break disulfide bonds. However, the unexpected surprising discovery is that there is no need for the removal of DTT in order to obtain a correct refolding of the protein. Contrary to the general knowledge that DTT has to be removed from the buffer in order for proteins to be refolded properly, it is surprisingly discovered by applicants that presence of DTT does not interfere with the refolding process in the high pressure treatment of present invention. The KSAC soluble proteins obtained from high pressure process of present invention were refolded correctly to form trimers in the presence of DTT.

Having thus described in detail preferred embodiments of the present invention, it is to be understood that the invention defined by the above examples is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

```
SEQUENCE LISTING

<160> NUMBER OF SEQ ID NOS: 6

<210> SEQ ID NO 1
<211> LENGTH: 3012
<212> TYPE: DNA
<213> ORGANISM: artificial sequence
<220> FEATURE:
<223> OTHER INFORMATION: KSAC DNA

<400> SEQUENCE: 1
atggccacca cgtacgagga gttttcggcg aagctggacc gcctggatga ggagttcaac       60
aggaagatgc aggagcagaa cgccaagttc tttgcggaca agccggatga gtcgacgctg      120
tcgcccgaga tgaaggagca ctacgagaag ttcgagcgca tgatcaagga acacacagag      180
aagttcaaca agaagatgca cgagcactcg gagcacttca agcagaagtt cgccgagctg      240
ctcgagcagc agaaggctgc gcagtacccg tccaagacta gttccgccgg tggccgtgag      300
accgcgccga cgaacctgat tcgtcgccgc aacaaggacg agacaaacgg ggatgtcagc      360
gccgccgccg accgcttccg cgaccgcttc gagaaggcaa ccctcgagga gcgcaaggcc      420
gccaccacga cgatggtcaa cgagtactac gacctggtga cggacttcta cgagtacggc      480
tggggccaga acttccattt cgcgccgcgc tacgccggcg agaccttctt cgagtccctc      540
gcgcgccacg agtacttcct ggccgctcgc ggcggcttca tggagggcga ccacatcgtc      600
gacgtgggct gcggcgtcgg cggtccggcg cgcaacatgg ttcgcctcac gcgctgcaac      660
gtcatcggcg tcaacaacaa cgattaccag atcagccgcg ctcgccgtca tgacgcgctc      720
gccggtatga gctccaagat cgactacgtc aagaccgact tctgcaacat gagcttagcc      780
gacaacacct tcgacggcgc ctacgccatc gaggccacct gccacgcaaa ggacaaggtc      840
aagtgctata gcgaggtctt ccgtgtcatc aagcccggca cctgctttgt cctgtacgag      900
tggtgcatga ccgacaagta caaccccaat gacgagtacc accgcacaat caagcaccgc      960
atcgagctgg gcgacggcct gccggagatg gagacgtgca acaggtgat cgagtacatg     1020 aagcaggccg gcttcgtggt ggaggaggcc atagacgtca tcagtcagtt cgagtccagc     1080
```

```
cccatcaaga gtatcccgtg gtaccagccg ctggtcggcg actattcgtc cctgcagggc    1140
ctgcgctcta ccccgattgg ccgcatcctc acgaacgtca tgtgtcgcgt gctggagttc    1200
gtgcgcctag ctccgaaggg cacgtacaag gcgacggaga ttttggagga ggctgcggaa    1260
agcctggtgg tgggcggtca gctcggcatc ttcacgccgt ccttctacat ccgcgctcgc    1320
aagccgtcca agcaggctgg atccaagatc cgcagcgtgc gtccgcttgt ggtgttgctg    1380
gtgtgcgtcg cggcggtgct cgcactcagc gcctccgctg agccgcacaa gcggccgtt     1440 gacgtcggcc cgctgagcgt tggcccgcag agcgtcggcc cgctgagcgt tggcccgcag    1500
gcggttggcc cgctgagcgt tggcccgcag agcgtcggcc cgctgagcgt tggcccgcag    1560
gcggttggcc cgctgagcgt tggcccgcag agcgttggcc cgctgagcgt tggcccgctg    1620
agcgttggcc cgcagagcgt tggcccgctg agcgttggca gccagagcgt cggcccgctg    1680
agcgttggtc cgcagagcgt cggcccgctg agcgttggcc cgcaggcggt tggcccgctg    1740
agcgttggcc cgcagagcgt cggcccgctg agcgttggcc cgcaggcggt tggcccgctg    1800
agcgttggcc cgcagagcgt cggcccgctg agcgttggcc cgcagagcgt tggcccgctg    1860
agcgttggca gccagagcgt cggcccgctg agcgttggtc cgcagagcgt cggcccgctg    1920
agcgttggcc cgcagagcgt cggcccgctg agcgttggcc cgcagagcgt cggcccgctg    1980
agcgttggtc cgcagagcgt tggcccgctg agcgttggcc cgcagagcgt tgacgttagc    2040
ccggtgagcg gatccgaatt cgatgcggtg gactggcgcg agaagggcgc cgtgacgccg    2100
gtgaagaatc aaggcgcgtg cgggtcgtgc tgggcgttct cggcggtcgg caacatcgag    2160
tcgcagtggg cccgtgccgg ccacggcttg gtgagcctgt cggagcagca gctggtgagc    2220
tgcgatgaca agacaatggc tgcaacggc gggctgatgc tgcaggcgtt cgagtggctg     2280
ctgcgacaca tgtacgggat cgtgttcacg gagaagagct accctacac gtccggcaac     2340 ggtgatgtgg ccgagtgctt gaacagcagt aaactcgttc ccggcgcgca aatcgacggc    2400
tacgtgatga tcccgagcaa cgaaacggtt atggctgcgt ggcttgcgga gatggccc     2460 atcgcgattg cggtcgacgc cagctccttc atgtcttacc agagcggcgt gctgaccagc    2520
tgcgctggcg atgcactgaa ccacggcgtg ctgctcgtcg gtacaacaa gaccggtggg     2580 gttccgtact gggtgatcaa gaactcgtgg ggtgaggact ggggcgagaa gggctacgtg    2640
cgcgtggtca tggggctgaa cgcgtgcctg ctcagtgaat accccgtgtc cgcgcatgtg    2700
ccgcggagtc tcaccccctgg cccgggcacg gagagcgagg agcgcgcccc taaacgggtg   2760
acggtggagc agatgatgtg caccgatatg tactgcaggg aggggtgcaa gaagagtctt    2820
ctcaccgcga acgtgtgcta caagaacggg ggaggcggct cctctatgac gaagtgcggt    2880
ccgcagaagg tgctgatgtg ctcgtactcg aaccctcatt gctttggtcc tgggctgtgc    2940
ctcgagactc ctgatggcaa gtgcgcgccg tacttcttgg gctcgatcat gaacacctgc    3000
cagtacacgt aa                                                      3012

<210> SEQ ID NO 2
<211> LENGTH: 1003
<212> TYPE: PRT
<213> ORGANISM: artificial sequence
<220> FEATURE:
<223> OTHER INFORMATION: KSAC protein

<400> SEQUENCE: 2

Met Ala Thr Thr Tyr Glu Glu Phe Ser Ala Lys Leu Asp Arg Leu Asp
1               5                   10                  15
```

```
Glu Phe Asn Arg Lys Met Gln Glu Gln Asn Ala Lys Phe Phe Ala
    20                  25                  30

Asp Lys Pro Asp Glu Ser Thr Leu Ser Pro Glu Met Lys Glu His Tyr
        35                  40                  45

Glu Lys Phe Glu Arg Met Ile Lys Glu His Thr Glu Lys Phe Asn Lys
    50                  55                  60

Lys Met His Glu His Ser Glu His Phe Lys Gln Lys Phe Ala Glu Leu
65                  70                  75                  80

Leu Glu Gln Gln Lys Ala Ala Gln Tyr Pro Ser Lys Thr Ser Ser Ala
                85                  90                  95

Gly Gly Arg Glu Thr Ala Pro Thr Asn Leu Ile Arg Arg Asn Lys
            100                 105                 110

Asp Glu Thr Asn Gly Asp Val Ser Ala Ala Asp Arg Phe Arg Asp
        115                 120                 125

Arg Phe Glu Lys Ala Thr Leu Glu Glu Arg Lys Ala Ala Thr Thr Thr
    130                 135                 140

Met Val Asn Glu Tyr Tyr Asp Leu Val Thr Asp Phe Tyr Glu Tyr Gly
145                 150                 155                 160

Trp Gly Gln Asn Phe His Phe Ala Pro Arg Tyr Ala Gly Glu Thr Phe
                165                 170                 175

Phe Glu Ser Leu Ala Arg His Glu Tyr Phe Leu Ala Ala Arg Gly Gly
            180                 185                 190

Phe Met Glu Gly Asp His Ile Val Asp Val Gly Cys Gly Val Gly Gly
        195                 200                 205

Pro Ala Arg Asn Met Val Arg Leu Thr Arg Cys Asn Val Ile Gly Val
        210                 215                 220

Asn Asn Asn Asp Tyr Gln Ile Ser Arg Ala Arg Arg His Asp Ala Leu
225                 230                 235                 240

Ala Gly Met Ser Ser Lys Ile Asp Tyr Val Lys Thr Asp Phe Cys Asn
                245                 250                 255

Met Ser Leu Ala Asp Asn Thr Phe Asp Gly Ala Tyr Ala Ile Glu Ala
            260                 265                 270

Thr Cys His Ala Lys Asp Lys Val Lys Cys Tyr Ser Glu Val Phe Arg
        275                 280                 285

Val Ile Lys Pro Gly Thr Cys Phe Val Leu Tyr Glu Trp Cys Met Thr
    290                 295                 300

Asp Lys Tyr Asn Pro Asn Asp Glu Tyr His Arg Thr Ile Lys His Arg
305                 310                 315                 320

Ile Glu Leu Gly Asp Gly Leu Pro Glu Met Glu Thr Cys Lys Gln Val
                325                 330                 335

Ile Glu Tyr Met Lys Gln Ala Gly Phe Val Val Glu Glu Ala Ile Asp
            340                 345                 350

Val Ile Ser Gln Phe Glu Ser Ser Pro Ile Lys Ser Ile Pro Trp Tyr
        355                 360                 365

Gln Pro Leu Val Gly Asp Tyr Ser Ser Leu Gln Gly Leu Arg Ser Thr
    370                 375                 380

Pro Ile Gly Arg Ile Leu Thr Asn Val Met Cys Arg Val Leu Glu Phe
385                 390                 395                 400

Val Arg Leu Ala Pro Lys Gly Thr Tyr Lys Ala Thr Glu Ile Leu Glu
                405                 410                 415

Glu Ala Ala Glu Ser Leu Val Val Gly Gly Gln Leu Gly Ile Phe Thr
            420                 425                 430
```

```
Pro Ser Phe Tyr Ile Arg Ala Arg Lys Pro Ser Lys Gln Ala Gly Ser
            435                 440                 445

Lys Ile Arg Ser Val Arg Pro Leu Val Val Leu Leu Val Cys Val Ala
450                 455                 460

Ala Val Leu Ala Leu Ser Ala Ser Ala Glu Pro His Lys Ala Ala Val
465                 470                 475                 480

Asp Val Gly Pro Leu Ser Val Gly Pro Gln Ser Val Gly Pro Leu Ser
            485                 490                 495

Val Gly Pro Gln Ala Val Gly Pro Leu Ser Val Gly Pro Gln Ser Val
            500                 505                 510

Gly Pro Leu Ser Val Gly Pro Gln Ala Val Gly Pro Leu Ser Val Gly
            515                 520                 525

Pro Gln Ser Val Gly Pro Leu Ser Val Gly Pro Leu Ser Val Gly Pro
            530                 535                 540

Gln Ser Val Gly Pro Leu Ser Val Gly Ser Gln Ser Val Gly Pro Leu
545                 550                 555                 560

Ser Val Gly Pro Gln Ser Val Gly Pro Leu Ser Val Gly Pro Gln Ala
                565                 570                 575

Val Gly Pro Leu Ser Val Gly Pro Gln Ser Val Gly Pro Leu Ser Val
            580                 585                 590

Gly Pro Gln Ala Val Gly Pro Leu Ser Val Gly Pro Gln Ser Val Gly
            595                 600                 605

Pro Leu Ser Val Gly Pro Gln Ser Val Gly Pro Leu Ser Val Gly Ser
            610                 615                 620

Gln Ser Val Gly Pro Leu Ser Val Gly Pro Gln Ser Val Gly Pro Leu
625                 630                 635                 640

Ser Val Gly Pro Gln Ser Val Gly Pro Leu Ser Val Gly Pro Gln Ser
                645                 650                 655

Val Gly Pro Leu Ser Val Gly Pro Gln Ser Val Gly Pro Leu Ser Val
            660                 665                 670

Gly Pro Gln Ser Val Asp Val Ser Pro Val Ser Gly Ser Glu Phe Asp
            675                 680                 685

Ala Val Asp Trp Arg Glu Lys Gly Ala Val Thr Pro Val Lys Asn Gln
690                 695                 700

Gly Ala Cys Gly Ser Cys Trp Ala Phe Ser Ala Val Gly Asn Ile Glu
705                 710                 715                 720

Ser Gln Trp Ala Arg Ala Gly His Gly Leu Val Ser Leu Ser Glu Gln
                725                 730                 735

Gln Leu Val Ser Cys Asp Asp Lys Asp Asn Gly Cys Asn Gly Gly Leu
            740                 745                 750

Met Leu Gln Ala Phe Glu Trp Leu Leu Arg His Met Tyr Gly Ile Val
            755                 760                 765

Phe Thr Glu Lys Ser Tyr Pro Tyr Thr Ser Gly Asn Gly Asp Val Ala
770                 775                 780

Glu Cys Leu Asn Ser Ser Lys Leu Val Pro Gly Ala Gln Ile Asp Gly
785                 790                 795                 800

Tyr Val Met Ile Pro Ser Asn Glu Thr Val Met Ala Ala Trp Leu Ala
                805                 810                 815

Glu Asn Gly Pro Ile Ala Ile Ala Val Asp Ala Ser Ser Phe Met Ser
            820                 825                 830

Tyr Gln Ser Gly Val Leu Thr Ser Cys Ala Gly Asp Ala Leu Asn His
            835                 840                 845

Gly Val Leu Leu Val Gly Tyr Asn Lys Thr Gly Gly Val Pro Tyr Trp
```

```
Val Ile Lys Asn Ser Trp Gly Glu Asp Trp Gly Lys Gly Tyr Val
865                 870                 875                 880

Arg Val Val Met Gly Leu Asn Ala Cys Leu Leu Ser Glu Tyr Pro Val
                885                 890                 895

Ser Ala His Val Pro Arg Ser Leu Thr Pro Gly Pro Gly Thr Glu Ser
                900                 905                 910

Glu Glu Arg Ala Pro Lys Arg Val Thr Val Glu Gln Met Met Cys Thr
            915                 920                 925

Asp Met Tyr Cys Arg Glu Gly Cys Lys Lys Ser Leu Leu Thr Ala Asn
        930                 935                 940

Val Cys Tyr Lys Asn Gly Gly Gly Ser Ser Met Thr Lys Cys Gly
945                 950                 955                 960

Pro Gln Lys Val Leu Met Cys Ser Tyr Ser Asn Pro His Cys Phe Gly
                965                 970                 975

Pro Gly Leu Cys Leu Glu Thr Pro Asp Gly Lys Cys Ala Pro Tyr Phe
                980                 985                 990

Leu Gly Ser Ile Met Asn Thr Cys  Gln Tyr Thr
        995                 1000
```

<210> SEQ ID NO 3
<211> LENGTH: 92
<212> TYPE: PRT
<213> ORGANISM: artificial sequence
<220> FEATURE:
<223> OTHER INFORMATION: KMP11 protein

<400> SEQUENCE: 3

```
Met Ala Thr Thr Tyr Glu Glu Phe Ser Ala Lys Leu Asp Arg Leu Asp
1               5                   10                  15

Glu Glu Phe Asn Arg Lys Met Gln Glu Gln Asn Ala Lys Phe Phe Ala
                20                  25                  30

Asp Lys Pro Asp Glu Ser Thr Leu Ser Pro Glu Met Lys Glu His Tyr
            35                  40                  45

Glu Lys Phe Glu Arg Met Ile Lys Glu His Thr Glu Lys Phe Asn Lys
        50                  55                  60

Lys Met His Glu His Ser Glu His Phe Lys Gln Lys Phe Ala Glu Leu
65                  70                  75                  80

Leu Glu Gln Gln Lys Ala Ala Gln Tyr Pro Ser Lys
                85                  90
```

<210> SEQ ID NO 4
<211> LENGTH: 352
<212> TYPE: PRT
<213> ORGANISM: artificial sequence
<220> FEATURE:
<223> OTHER INFORMATION: SMT protein

<400> SEQUENCE: 4

```
Ser Ala Gly Gly Arg Glu Thr Ala Pro Thr Asn Leu Ile Arg Arg
1               5                   10                  15

Asn Lys Asp Glu Thr Asn Gly Asp Val Ser Ala Ala Ala Asp Arg Phe
                20                  25                  30

Arg Asp Arg Phe Glu Lys Ala Thr Leu Glu Glu Arg Lys Ala Ala Thr
            35                  40                  45

Thr Thr Met Val Asn Glu Tyr Tyr Asp Leu Val Thr Asp Phe Tyr Glu
        50                  55                  60
```

Tyr Gly Trp Gly Gln Asn Phe His Phe Ala Pro Arg Tyr Ala Gly Glu
65                  70                  75                  80

Thr Phe Phe Glu Ser Leu Ala Arg His Glu Tyr Phe Leu Ala Ala Arg
                85                  90                  95

Gly Gly Phe Met Glu Gly Asp His Ile Val Asp Val Gly Cys Gly Val
            100                 105                 110

Gly Gly Pro Ala Arg Asn Met Val Arg Leu Thr Arg Cys Asn Val Ile
        115                 120                 125

Gly Val Asn Asn Asn Asp Tyr Gln Ile Ser Arg Ala Arg Arg His Asp
    130                 135                 140

Ala Leu Ala Gly Met Ser Ser Lys Ile Asp Tyr Val Lys Thr Asp Phe
145                 150                 155                 160

Cys Asn Met Ser Leu Ala Asp Asn Thr Phe Asp Gly Ala Tyr Ala Ile
                165                 170                 175

Glu Ala Thr Cys His Ala Lys Asp Lys Val Lys Cys Tyr Ser Glu Val
            180                 185                 190

Phe Arg Val Ile Lys Pro Gly Thr Cys Phe Val Leu Tyr Glu Trp Cys
        195                 200                 205

Met Thr Asp Lys Tyr Asn Pro Asn Asp Glu Tyr His Arg Thr Ile Lys
    210                 215                 220

His Arg Ile Glu Leu Gly Asp Gly Leu Pro Glu Met Glu Thr Cys Lys
225                 230                 235                 240

Gln Val Ile Glu Tyr Met Lys Gln Ala Gly Phe Val Val Glu Glu Ala
                245                 250                 255

Ile Asp Val Ile Ser Gln Phe Glu Ser Ser Pro Ile Lys Ser Ile Pro
            260                 265                 270

Trp Tyr Gln Pro Leu Val Gly Asp Tyr Ser Ser Leu Gln Gly Leu Arg
        275                 280                 285

Ser Thr Pro Ile Gly Arg Ile Leu Thr Asn Val Met Cys Arg Val Leu
    290                 295                 300

Glu Phe Val Arg Leu Ala Pro Lys Gly Thr Tyr Lys Ala Thr Glu Ile
305                 310                 315                 320

Leu Glu Glu Ala Ala Glu Ser Leu Val Val Gly Gly Gln Leu Gly Ile
                325                 330                 335

Phe Thr Pro Ser Phe Tyr Ile Arg Ala Arg Lys Pro Ser Lys Gln Ala
            340                 345                 350

<210> SEQ ID NO 5
<211> LENGTH: 235
<212> TYPE: PRT
<213> ORGANISM: artificial sequence
<220> FEATURE:
<223> OTHER INFORMATION: A2 protein

<400> SEQUENCE: 5

Lys Ile Arg Ser Val Arg Pro Leu Val Val Leu Leu Val Cys Val Ala
1               5                   10                  15

Ala Val Leu Ala Leu Ser Ala Ser Ala Glu Pro His Lys Ala Ala Val
                20                  25                  30

Asp Val Gly Pro Leu Ser Val Gly Pro Gln Ser Val Gly Pro Leu Ser
            35                  40                  45

Val Gly Pro Gln Ala Val Gly Pro Leu Ser Val Gly Pro Gln Ser Val
        50                  55                  60

Gly Pro Leu Ser Val Gly Pro Gln Ala Val Gly Pro Leu Ser Val Gly
65                  70                  75                  80

```
Pro Gln Ser Val Gly Pro Leu Ser Val Gly Pro Leu Ser Val Gly Pro
                85                  90                  95

Gln Ser Val Gly Pro Leu Ser Val Gly Ser Gln Ser Val Gly Pro Leu
            100                 105                 110

Ser Val Gly Pro Gln Ser Val Gly Pro Leu Ser Val Gly Pro Gln Ala
        115                 120                 125

Val Gly Pro Leu Ser Val Gly Pro Gln Ser Val Gly Pro Leu Ser Val
    130                 135                 140

Gly Pro Gln Ala Val Gly Pro Leu Ser Val Gly Pro Gln Ser Val Gly
145                 150                 155                 160

Pro Leu Ser Val Gly Pro Gln Ser Val Gly Pro Leu Ser Val Gly Ser
            165                 170                 175

Gln Ser Val Gly Pro Leu Ser Val Gly Pro Gln Ser Val Gly Pro Leu
        180                 185                 190

Ser Val Gly Pro Gln Ser Val Gly Pro Leu Ser Val Gly Pro Gln Ser
    195                 200                 205

Val Gly Pro Leu Ser Val Gly Pro Gln Ser Val Gly Pro Leu Ser Val
    210                 215                 220

Gly Pro Gln Ser Val Asp Val Ser Pro Val Ser
225                 230                 235

<210> SEQ ID NO 6
<211> LENGTH: 316
<212> TYPE: PRT
<213> ORGANISM: artificial sequence
<220> FEATURE:
<223> OTHER INFORMATION: CBP protein

<400> SEQUENCE: 6

Asp Ala Val Asp Trp Arg Glu Lys Gly Ala Val Thr Pro Val Lys Asn
1               5                   10                  15

Gln Gly Ala Cys Gly Ser Cys Trp Ala Phe Ser Ala Val Gly Asn Ile
            20                  25                  30

Glu Ser Gln Trp Ala Arg Ala Gly His Gly Leu Val Ser Leu Ser Glu
        35                  40                  45

Gln Gln Leu Val Ser Cys Asp Asp Lys Asp Asn Gly Cys Asn Gly Gly
    50                  55                  60

Leu Met Leu Gln Ala Phe Glu Trp Leu Leu Arg His Met Tyr Gly Ile
65                  70                  75                  80

Val Phe Thr Glu Lys Ser Tyr Pro Tyr Thr Ser Gly Asn Gly Asp Val
                85                  90                  95

Ala Glu Cys Leu Asn Ser Ser Lys Leu Val Pro Gly Ala Gln Ile Asp
            100                 105                 110

Gly Tyr Val Met Ile Pro Ser Asn Glu Thr Val Met Ala Ala Trp Leu
        115                 120                 125

Ala Glu Asn Gly Pro Ile Ala Ile Ala Val Asp Ala Ser Ser Phe Met
    130                 135                 140

Ser Tyr Gln Ser Gly Val Leu Thr Ser Cys Ala Gly Asp Ala Leu Asn
145                 150                 155                 160

His Gly Val Leu Leu Val Gly Tyr Asn Lys Thr Gly Gly Val Pro Tyr
                165                 170                 175

Trp Val Ile Lys Asn Ser Trp Gly Glu Asp Trp Gly Glu Lys Gly Tyr
            180                 185                 190

Val Arg Val Val Met Gly Leu Asn Ala Cys Leu Leu Ser Glu Tyr Pro
        195                 200                 205
```

-continued

| | | | | | | | | | | | | | |
|---|---|---|---|---|---|---|---|---|---|---|---|---|---|
| Val | Ser<br>210 | Ala | His | Val | Pro<br>215 | Arg | Ser | Leu | Thr<br>220 | Pro | Gly | Thr | Glu |
| Ser<br>225 | Glu | Glu | Arg | Ala | Pro<br>230 | Lys | Arg | Val | Thr<br>235 | Val | Glu | Gln | Met | Met | Cys<br>240 |
| Thr | Asp | Met | Tyr | Cys<br>245 | Arg | Glu | Gly | Cys | Lys<br>250 | Lys | Ser | Leu | Leu<br>255 | Thr | Ala |
| Asn | Val | Cys | Tyr<br>260 | Lys | Asn | Gly | Gly | Gly<br>265 | Gly | Ser | Ser | Met | Thr<br>270 | Lys | Cys |
| Gly | Pro | Gln<br>275 | Lys | Val | Leu | Met | Cys<br>280 | Ser | Tyr | Ser | Asn | Pro<br>285 | His | Cys | Phe |
| Gly | Pro<br>290 | Gly | Leu | Cys | Leu | Glu<br>295 | Thr | Pro | Asp | Gly | Lys<br>300 | Cys | Ala | Pro | Tyr |
| Phe<br>305 | Leu | Gly | Ser | Ile | Met<br>310 | Asn | Thr | Cys | Gln | Tyr<br>315 | Thr |

What we claim is:

1. A composition comprising (i) a refolded and solubilized fusion protein and (ii) dithiothreitol (DTT), wherein the fusion protein consists of *leishmania* antigens Kin